US010982121B2

(12) United States Patent
Chung

(10) Patent No.: US 10,982,121 B2
(45) Date of Patent: Apr. 20, 2021

(54) ZWITTERIONIC CROSSLINKED POLYMER-BASED ADHESIVES

(71) Applicant: The Florida State University Research Foundation, Inc., Tallahassee, FL (US)

(72) Inventor: Hoyong Chung, Tallahassee, FL (US)

(73) Assignee: THE FLORIDA STATE UNIVERSITY RESEARCH FOUNDATION, INC., Tallahassee, FL (US)

( * ) Notice: Subject to any disclaimer, the term of this patent is extended or adjusted under 35 U.S.C. 154(b) by 7 days.

(21) Appl. No.: 16/386,976

(22) Filed: Apr. 17, 2019

(65) Prior Publication Data

US 2020/0332161 A1 Oct. 22, 2020

(51) Int. Cl.
| | |
|---|---|
| *C08F 2/46* | (2006.01) |
| *C08F 2/50* | (2006.01) |
| *C08G 61/04* | (2006.01) |
| *C09J 133/14* | (2006.01) |
| *C09J 133/26* | (2006.01) |
| *C09J 11/06* | (2006.01) |
| *A61L 24/06* | (2006.01) |
| *A61L 24/10* | (2006.01) |
| *C09J 11/08* | (2006.01) |
| *C08K 5/11* | (2006.01) |

(52) U.S. Cl.
CPC ............ *C09J 133/14* (2013.01); *A61L 24/06* (2013.01); *A61L 24/10* (2013.01); *C09J 11/06* (2013.01); *C09J 11/08* (2013.01); *C09J 133/26* (2013.01); *C08K 5/11* (2013.01)

(58) Field of Classification Search
CPC ... C08F 2/45; C08F 8/30; C08G 61/04; A61K 47/48; C08L 77/00
USPC .......... 522/175, 174, 173, 1; 520/1; 525/180
See application file for complete search history.

(56) References Cited

PUBLICATIONS

Glass et al, Enhanced Wet Adhesion and Shear of Eleastomeric Micro-Fiber Arrays with Mushroom Tip Geometry and a Photopolymerized p(DMA-co-MEA) tip coating, Sep. 29, 2010, Langmuir, 26(22), 17357-17362 (Year: 2010).*
Zhu et al, The synthesis and aqueous solution properties of sulfobutylbetaine (co)polymers: comparison of synthetic routes and tuneable upper critical solution temperatures, Apr. 15, 2015, Polym. Chem., 6, 5705-5718 (Year: 2015).*
Kim et al, Photo-reponsive bio-inspired adhesives: facile control of adhesion strength via photocleavable crosslinker, Sep. 25, 2017, Poly. Chem., 8, 6300-6308 (Year: 2017).*
Kim et al (Lee et al), synthesis of lightly crosslinked zwitterionic polymer-based bioinspired adhesives for intestinal tissue sealing, May 11, 2018, Journal of polymer science, part A: polymer chemistry, 56, 1564-1573 (Year: 2018).*
Agard, Nicholas J., Jennifer A. Prescher, and Carolyn R. Bertozzi. "A strain-promoted [3+2] azide—alkyne cycloaddition for covalent modification of biomolecules in living systems." Journal of the American Chemical Society 126.46 (2004): 15046-15047.
Ahn, B. Kollbe, et al. "High-performance mussel-inspired adhesives of reduced complexity." Nature communications 6 (2015): 8663.
Ahn, B. Kollbe, et al. "Surface-initiated self-healing of polymers in aqueous media." Nature materials 13.9 (2014): 867.
Albertin, Luca, et al. "Chemoenzymatic synthesis of narrow-polydispersity glycopolymers: Poly (6-O-vinyladipoyl-D-lucopyranose)." Biomacromolecules 5.2 (2004): 255-260.
Aoi, Keigo, et al. "First synthesis of glycopeptide macromonomers and graft-type sugar-containing polymers with glycopeptide side chains." Macromolecules 29.12 (1996): 4456-4458.
Asahara, Junko, et al. "Crosslinked acrylic pressure-sensitive adhesives. I. Effect of the crosslinking reaction on the peel strength." Journal of applied polymer science 87.9 (2003): 1493-1499.
Azagarsamy, Malar A., et al. "Coumarin-based photodegradable hydrogel: Design, synthesis, gelation, and degradation kinetics." ACS Macro Letters 3.6 (2014): 515-519.
Banea, M. D., et al. "Debonding on command of multi-material adhesive joints." The Journal of Adhesion 93.10 (2017): 756-770.
Banea, M., L. F. M. da Silva, and R. D. S. G. Campilho. "An overview of the technologies for adhesive debonding on command." Annals of "Dunarea de Jos" University of Galati. Fascicle XII: Welding Equipment and Technology 24 (2013): 11-14.
Banea, Mariana D., et al. "Smart adhesive joints: An overview of recent developments" The Journal of Adhesion 90.1 (2014): 16-40.
Barbero, Ana M., and H. Frederick Frasch. "Pig and guinea pig skin as surrogates for human in vitro penetration studies: a quantitative review." Toxicology in vitro 23.1 (2009): 1-13.
Beal, David M., and Lyn H. Jones. "Molecular scaffolds using multiple orthogonal conjugations: applications in chemical biology and drug discovery." Angewandte Chemie International Edition 51.26 (2012): 6320-6326.
Bertozzi, Carolyn R. "A decade of bioorthogonal chemistry." (2011): 651-653.
Bhagat, Vrushali, and Matthew L. Becker. "Degradable adhesives for surgery and tissue engineering." Biomacromolecules 18.10 (2017): 3009-3039.
Bilic, et al., "Injectable candidate sealants for fetal membrane repair: bonding and toxicity in vitro", Am. J. Obstet. Gynecol. 2010, 202, 85.e81-85.e89.
BioGlue surgical adhesive instructions for use. BioGlue Surgical Adhesive Instructions for Use; CyroLife, Ed.: Kennesaw, 2010. 16 pages.
Black, Kvar CL, et al. "Polydopamine-enabled surface functionalization of gold nanorods for cancer cell-targeted imaging and photothermal therapy." Nanomedicine 8.1 (2013): 17-28.

(Continued)

*Primary Examiner* — Jessica Whiteley
(74) *Attorney, Agent, or Firm* — Meunier Carlin & Curfman LLC

(57) ABSTRACT

Disclosed are terpolymer adhesives comprising three different repeating domains: a catechol containing domain, a zwitterionic domain, and a crosslinking domain. In specific examples, the polymer can contain a 3,4-dihydroxy-L-phenylalanine (DOPA) segment which contains a catechol group, a poly(sulfobetaine methacrylate) (polySBMA), and poly(ethylene glycol) dimethacrylate (PEGDMA) for light crosslinking. Alternatively, a photocleavable nitrobenzyloxycarbonyl containing crosslinker can be used. The disclosed polymers can be used as biomedical adhesives, such as to prevent leakage from the sutured intestinal tissue.

14 Claims, 10 Drawing Sheets

(56) References Cited

PUBLICATIONS

Bouten, Petra JM, et al. "The chemistry of tissue adhesive materials." Progress in Polymer Science39.7 (2014): 1375-1405.

Brown, Tobin E., Ian A. Marozas, and Kristi S. Anseth. "AmplifiedPhotodegradation of Cell-Laden Hydrogels via an Addition—Fragmentation Chain Transfer Reaction." Advanced Materials 29.11 (2017): 1605001.

Brubaker, Carrie E., et al. "Biological performance of mussel-inspired adhesive in extrahepatic islet transplantation." Biomaterials 31.3 (2010): 420-427.

Burks, Sandra, and William Spotnitz. "Safety and usability of hemostats, sealants, and adhesives." AORN journal 100.2 (2014): 160-176.

Callow, James A., and Maureen E. Callow. "Trends in the development of environmentally friendly fouling-resistant marine coatings." Nature communications 2 (2011): 244.

Cao, Zhigiang, Lei Zhang, and Shaoyi Jiang. "Superhydrophilic zwitterionic polymers stabilize liposomes." Langmuir 28.31 (2012): 11625-11632.

Chang, Jing, et al. "An in situ-forming zwitterionic hydrogel as vitreous substitute." Journal of Materials Chemistry B 3.6 (2015): 1097-1105.

Chang, Yung, et al. "A highly stable nonbiofouling surface with well-packed grafted zwitterionic polysulfobetaine for plasma protein repulsion." Langmuir 24.10 (2008): 5453-5458.

Chen, Shengfu, et al. "Strong resistance of phosphorylcholine self-assembled monolayers to protein adsorption: insights into nonfouling properties of zwitterionic materials." Journal of the American Chemical Society 127.41 (2005): 14473-14478.

Ch'Ng, Hung Seng, et al. "Bioadhesive polymers as platforms for oral controlled drug delivery II: synthesis and evaluation of some swelling, water-insoluble bioadhesive polymers." Journal of pharmaceutical sciences 74.4 (1985): 399-405.

Choi, Gun Young, Walter Zurawsky, and Abraham Ulman. "Molecular weight effects in adhesion." Langmuir 15.24 (1999): 8447-8450.

Chung, Hoyong, and Robert H. Grubbs. "Rapidly cross-linkable DOPA containing terpolymer adhesives and PEG-based cross-linkers for biomedical applications." Macromolecules 45.24 (2012): 9666-9673.

Chung, Hoyong, et al. "Enhanced adhesion of dopamine methacrylamide elastomers via viscoelasticity tuning." Biomacromolecules 12.2 (2010): 342-347.

Cimen, Dilek, Ertan Yildirim, and Tuncer Caykara. "Synthesis of dual-functional poly (6-azidohexylmethacrylate) brushes by a RAFT agent carrying carboxylic acid end groups." Journal of Polymer Science Part A: Polymer Chemistry 53.14 (2015): 1696-1706.

Corrie, John et, al. "Photolytic cleavage of 1-(2-nitrophenyl) ethyl ethers involves two parallel pathways and product release is rate-limited by decomposition of a common hemiacetal intermediate." Journal of the American Chemical Society 125.28 (2003): 8546-8554.

Dai, Mengzhen, et al. "Immobilization of enzymes by electrochemical and chemical oxidative polymerization of L-DOPA to fabricate amperometric biosensors and biofuel cells." ACS applied materials & interfaces 7.20 (2015): 10843-10852.

Debets, Marjoke F., et al. "Bioconjugation with strained alkenes and alkynes." Accounts of chemical research 44.9 (2011): 805-815.

Delgado, Jose D., and Joseph B. Schlenoff. "Static and dynamic solution behavior of a polyzwitterion using a Hofmeister salt series." Macromolecules50.11 (2017): 4454-4464.

Faure, Emilie, et al. "Catechols as versatile platforms in polymer chemistry." Progress in polymer science 38.1 (2013): 236-270.

Fratila, Raluca M., et al. "Covalent immobilisation of magnetic nanoparticles on surfaces via strain-promoted azide-alkyne click chemistry." New Journal of Chemistry 41.19 (2017): 10835-10840.

Furuike, Tetsuya, et al. "Synthetic glycoconjugates. 6. Preparation and biochemical evaluation of novel cluster-type glycopolymers containing Gal. beta.(1. fwdarw. 4) GlcNAc (N-Acetyllactosamine) residue." Macromolecules 28.21 (1995): 7241-7247.

Ganda, Sylvia, et al. "Biodegradable glycopolymeric micelles obtained by RAFT-controlled radical ring-opening polymerization." Macromolecules 49.11 (2016): 4136-4146.

Gent, A. N. "Adhesion and strength of viscoelastic solids. Is there a relationship between adhesion and bulk properties?" Langmuir 12.19 (1996): 4492-4496.

Ghobril, C., and M. W. Grinstaff. "The chemistry and engineering of polymeric hydrogel adhesives for wound closure: a tutorial." Chemical Society Reviews 44.7 (2015): 1820-1835.

Gierenz and W. Karmann, in Adhesives and Adhesive Tapes, eds. G. Gierenz and W. Karmann, Wiley-VCH, Weinheim, 2008, ch. 1, pp. 1-95.

Glass, Paul, et al. "Enhanced wet adhesion and shear of elastomeric micro-fiber arrays with mushroom tip geometry and a photopolymerized p (DMA-co-MEA) tip coating." Langmuir 26.22 (2010): 17357-17362.

Gotz, Heide, et al. "Synthesis of lipo-glycopolymer amphiphiles by nitroxide-mediated living free-radical polymerization." Journal of Polymer Science Part A: Polymer Chemistry 40.20 (2002): 3379-3391.

Griffin, Donald R., and Andrea M. Kasko. "Photodegradable macromers and hydrogels for live cell encapsulation and release." Journal of the American chemical society 134.31 (2012): 13103-13107.

Griffin, Donald R., et al. "Synthesis of photodegradable macromers for conjugation and release of bioactive molecules." Biomacromolecules 14.4 (2013): 1199-1207.

Griffin, Donald R., Joseph T. Patterson, and Andrea M. Kasko. "Photodegradation as a mechanism for controlled drug delivery." Biotechnology and bioengineering 107.6 (2010): 1012-1019.

Guillier, Fabrice, David Orain, and Mark Bradley. "Linkers and cleavage strategies in solid-phase organic synthesis and combinatorial chemistry." Chemical Reviews 100.6 (2000): 2091-2158.

Guo, Jinshan, et al. "Click chemistry improved wet adhesion strength of mussel-inspired citrate-based antimicrobial bioadhesives." Biomaterials 112 (2017): 275-286.

Han, Dehui, Xia Tong, and Yue Zhao. "Fast photodegradable block copolymer micelles for burst release." Macromolecules 44.3 (2011): 437-439.

Han, Seulgi, et al. "Upconversion Nanoparticles/Hyaluronate—Rose Bengal Conjugate Complex for Noninvasive Photochemical Tissue Bonding." ACS nano 11.10 (2017): 9979-9988.

Harper, Tristan, et al. "Single-Phase Photo-Cross-Linkable Bioinspired Adhesive for Precise Control of Adhesion Strength." ACS applied materials & interfaces 9.2 (2017): 1830-1839.

Haydon, Donald. "ElectRelease—electrically disbonding epoxy adhesive." Assembly Automation 22.4 (2002): 326-329.

Hodgson, Sabrina M., et al. "Reproducible Dendronized PEG Hydrogels via SPAAC Cross-Linking." Biomacromolecules 18.12 (2017): 4054-4059.

Hwang, Dong Soo, et al. "Practical recombinant hybrid mussel bioadhesive fp-151." Biomaterials 28.24 (2007): 3560-3568.

Il'ichev, Yuri V., Markus A. Schwörer, and Jakob Wirz. "Photochemical reaction mechanisms of 2-nitrobenzyl compounds: methyl ethers and caged ATP." Journal of the American Chemical Society 126.14 (2004): 4581-4595.

Jadhav, K. R., A. Y. Pawar, and G. S. Talele. "Bioadhesive drug delivery system: An overview." Asian Journal of Pharmaceutical and clinical research 6.2 (2013): 1-10.

Jenkins, Courtney L., Heather J. Meredith, and Jonathan J. Wilker. "Molecular weight effects upon the adhesive bonding of a mussel mimetic polymer." ACS applied materials & interfaces 5.11 (2013): 5091-5096.

Jenkins, Courtney L., Heather M. Siebert, and Jonathan J. Wilker. "Integrating mussel chemistry into a bio-based polymer to create degradable adhesives." Macromolecules 50.2 (2017): 561-568.

Jiang, Shaoyi, and Zhigiang Cao. "Ultralow-fouling, functionalizable, and hydrolyzable zwitterionic materials and their derivatives for biological applications." Advanced materials 22.9 (2010): 920-932.

Jiao, et al., "Recent progresses in bioadhesive microspheres via transmucosaladministration", Colloids Surf., B, 2016, 140, 361-372.

(56) References Cited

PUBLICATIONS

Jin, X., et al. "Properties of solvent-borne acrylic pressure-sensitive adhesives synthesized by a simple approach." Exp. Pol. Let 3 (2009): 814-820.

Johnson, Jeremiah A., et al. "Synthesis of photocleavable linear macromonomers by ATRP and star macromonomers by a tandem ATRP—click reaction: Precursors to photodegradable model networks." Macromolecules 40.10 (2007): 3589-3598.

Kalva, Nagendra, Nimisha Parekh, and Ashootosh V. Ambade. "Controlled micellar disassembly of photo-and pH-cleavable linear-dendritic block copolymers." Polymer Chemistry 6.38 (2015): 6826-6835.

Käpylä, Elli, Stephanie M. Delgado, and Andrea M. Kasko. "Shape-changing photodegradable hydrogels for dynamic 3D cell culture." ACS applied materials & interfaces 8.28 (2016): 17885-17893.

Keefe, Andrew J., and Shaoyi Jiang. "Poly (zwitterionic) protein conjugates offer increased stability without sacrificing binding affinity or bioactivity." Nature chemistry 4.1 (2012): 59.

Kim, Hyo Jeong, et al. "Mussel adhesion-employed water-immiscible fluid bioadhesive for urinary fistula sealing." Biomaterials 72 (2015): 104-111.

Kim, Hyo Jeong, et al. "Sandcastle Worm-Inspired Blood-Resistant Bone Graft Binder Using a Sticky Mussel Protein for Augmented In Vivo Bone Regeneration." Advanced healthcare materials 5.24 (2016): 3191-3202.

Kim, Kyuri, et al. "Chitosan-catechol: A polymer with long-lasting mucoadhesive properties." Biomaterials 52 (2015): 161-170.

Kim, Minkyu, and Hoyong Chung. "Photo-responsive bio-inspired adhesives: facile control of adhesion strength via a photocleavable crosslinker." Polymer Chemistry 8.40 (2017): 6300-6308.

Kirschner, Chelsea M., et al. "Clickable, photodegradable hydrogels to dynamically modulate valvular interstitial cell phenotype." Advanced healthcare materials 3.5 (2014): 649-657.

Kivelio, A., et al. "Mussel mimetic tissue adhesive for fetal membrane repair: initial in vivo investigation in rabbits." European Journal of Obstetrics & Gynecology and Reproductive Biology 171.2 (2013): 240-245.

Kloxin, April M., et al. "Photodegradable hydrogels for dynamic tuning of physical and chemical properties." Science 324.5923 (2009): 59-63.

Kloxin, April M., et al. "Tunable hydrogels for external manipulation of cellular microenvironments through controlled photodegradation." Advanced Materials 22.1 (2010): 61-66.

Kloxin, Apr. M., Mark W. Tibbitt, and Kristi S. Anseth. "Synthesis of photodegradable hydrogels as dynamically tunable cell culture platforms." Nature protocols 5.12 (2010): 1867.

Kobayashi, Masanori, Takayuki Koide, and Suong-Hyu Hyon. "Tribological characteristics of polyethylene glycol (PEG) as a lubricant for wear resistance of ultra-high-molecular-weight polyethylene (UHMWPE) in artificial knee join." Journal of the mechanical behavior of biomedical materials 38 (2014): 33-38.

Kolb, Hartmuth C., M. G. Finn, and K. Barry Sharpless. "Click chemistry: diverse chemical function from a few good reactions." Angewandte Chemie International Edition 40.11 (2001): 2004-2021.

Kommu, Sashi S., et al. "Current status of hemostatic agents and sealants in urologic surgical practice." Reviews in urology 17.3 (2015): 150.

Kong, Rong, and Rohit Bhargava. "Characterization of porcine skin as a model for human skin studies using infrared spectroscopic imaging." Analyst 136.11 (2011): 2359-2366.

Kord Forooshani, Pegah, and Bruce P. Lee. "Recent approaches in designing bioadhesive materials inspired by mussel adhesive protein." Journal of Polymer Science Part A: Polymer Chemistry 55.1 (2017): 9-33.

Ladmiral, Vincent, et al. "Synthesis of neoglycopolymers by a combination of "click chemistry" and living radical polymerization." Journal of the American Chemical Society 128.14 (2006): 4823-4830.

Lalani, Reza, and Lingyun Liu. "Electrospun zwitterionic poly (sulfobetaine methacrylate) for nonadherent, superabsorbent, and antimicrobial wound dressing applications." Biomacromolecules 13.6 (2012): 1853-1863.

Lee, Bruce P., and Shari Konst. "Novel hydrogel actuator inspired by reversible mussel adhesive protein chemistry." Advanced Materials 26.21 (2014): 3415-3419.

Lee, Bruce P., et al. "Mussel-inspired adhesives and coatings." Annual review of materials research 41 (2011): 99-132.

Lee, Michele E., and Andrea M. Armani. "Flexible UV exposure sensor based on UV responsive polymer." ACS Sensors 1.10 (2016): 1251-1255.

Lee, Michele E., Eda Gungor, and Andrea M. Armani. "Photocleavage of poly (methyl acrylate) with centrally located o-nitrobenzyl moiety: influence of environment on kinetics." Macromolecules 48.24 (2015): 8746-8751.

Lee, Ted T., et al. "Light-triggered in vivo activation of adhesive peptides regulates cell adhesion, inflammation and vascularization of biomaterials." Nature materials 14.3 (2015): 352.

Leijonmarck, Simon, et al. "Electrochemical characterization of electrically induced adhesive debonding." Journal of the Electrochemical Society 158.10 (2011): P109-P114.

Leijonmarck, Simon, et al. "Electrolytically assisted debonding of adhesives: An experimental investigation." International Journal of Adhesion and Adhesives 32 (2012): 39-45.

Li, Lin, et al. "Injectable self-healing hydrogel with antimicrobial and antifouling properties." ACS applied materials & interfaces 9.11 (2017): 9221-9225.

Li, Yan-Fang, et al. "Light responsive hybrid nanofibres for on-demand therapeutic drug and cell delivery." Journal of tissue engineering and regenerative medicine 11.8 (2017): 2411-2420.

Lim, Seonghye, et al. "The adhesive properties of coacervated recombinant hybrid mussel adhesive proteins." Biomaterials 31.13 (2010): 3715-3722.

Ling, Daishun, et al. "Multiple-Interaction Ligands Inspired by Mussel Adhesive Protein: Synthesis of Highly Stable and Biocompatible Nanoparticles." Angewandte Chemie International Edition 50.48 (2011): 11360-11365.

Liu, Jenny, et al. ""Brush-first" method for the parallel synthesis of photocleavable, nitroxide-labeled poly (ethylene glycol) star polymers." Journal of the American Chemical Society 134.39 (2012): 16337-16344.

Liu, Qingsheng, et al. "A facile method of using sulfobetaine-containing copolymers for biofouling resistance." Journal of Applied Polymer Science 131.18 (2014), 40789.

Loizou, et al., "Structural Effects of Crosslinking a Biopolymer Hydrogel Derived from Marine Mussel Adhesive Protein", Macromol. Biosci., 2006, 6, 711-718.

Lovecka, Petra, et al. "Study of cytotoxic effects of benzonitrile pesticides." BioMed research international 2015, Article ID 381264, 9 pages.

Lowe, Andrew B., and Charles L. McCormick. "Synthesis and solution properties of zwitterionic polymers." Chemical reviews 102.11 (2002): 4177-4190.

Lowe, Andrew B., Brent S. Sumerlin, and Charles L. McCormick. "The direct polymerization of 2-methacryloxyethyl glucoside via aqueous reversible addition—fragmentation chain transfer (RAFT) polymerization." Polymer 44.22 (2003): 6761-6765.

Loykulnant, Surapich, and Akira Hirao. "Protection and polymerization of functional monomers. 30. Anionic living polymerization of 4-alkylstyrenes containing acetal-protected monosaccharide residues." Macromolecules 33.13 (2000): 4757-4764.

Lu, Dedai, et al. "Mussel-inspired thermoresponsive polypeptide—pluronic copolymers for versatile surgical adhesives and hemostasis." ACS applied materials & interfaces 9.20 (2017): 16756-16766.

Lu, Yuchen, James Broughton, and Pat Winfield. "A review of innovations in disbonding techniques for repair and recycling of automotive vehicles." International Journal of Adhesion and Adhesives 50 (2014): 119-127.

Maier, Greg P., et al. "Adaptive synergy between catechol and lysine promotes wet adhesion by surface salt displacement." Science 349.6248 (2015): 628-632.

(56) References Cited

PUBLICATIONS

Mandell, Samuel P., and Nicole S. Gibran. "Fibrin sealants: surgical hemostat, sealant and adhesive." Expert opinion on biological therapy 14.6 (2014): 821-830.
Manning, David D., et al. "Synthesis of sulfated neoglycopolymers: selective P-selectin inhibitors." Journal of the American Chemical Society 119.13 (1997): 3161-3162.
Manova, Radostina, Teris A. van Beek, and Han Zuilhof. "Surface Functionalization by Strain-Promoted Alkyne—Azide Click Reactions." Angewandte Chemie International Edition 50.24 (2011): 5428-5430.
Mateescu, Anca, et al. "Synthesis and characterization of novel glycosurfaces by ATRP." Soft Matter 5.8 (2009): 1621-1629.
Matos-Pérez, Cristina R., James D. White, and Jonathan J. Wilker. "Polymer composition and substrate influences on the adhesive bonding of a biomimetic, cross-linking polymer." Journal of the American Chemical Society 134.22 (2012): 9498-9505.
Matteini, Paolo, et al. "Light-responsive nanocomposite sponges for on demand chemical release with high spatial and dosage control." Journal of Materials Chemistry B 1.8 (2013): 1096-1100.
Matthiessen, Peter, et al. "Defunctioning stoma reduces symptomatic anastomotic leakage after low anterior resection of the rectum for cancer: a randomized multicenter trial." Annals of surgery 246.2 (2007): 207-214.
McKinnon, Daniel D., et al. "Design and characterization of a synthetically accessible, photodegradable hydrogel for user-directed formation of neural networks." Biomacromolecules 15.7 (2014): 2808-2816.
Mehdizadeh, Mohammadreza, and Jian Yang. "Design strategies and applications of tissue bioadhesives." Macromolecular bioscience 13.3 (2013): 271-288.
Meldal, Morten, and Christian Wenzel Tornøe. "Cu-catalyzed azide-alkyne cycloaddition." Chemical reviews 108.8 (2008): 2952-3015.
Mian, Shabeer A., et al. "Adsorption of catechol on a wet silica surface: density functional theory study." Theoretical Chemistry Accounts 130.2-3 (2011): 333-339.
Mian, Shabeer A., et al. "Density functional theory study of catechol adhesion on silica surfaces." The Journal of Physical Chemistry C 114.48 (2010): 20793-20800.
Michal, Brian T., Emily J. Spencer, and Stuart J. Rowan. "Stimuli-responsive reversible two-level adhesion from a structurally dynamic shape-memory polymer." ACS applied materials & interfaces 8.17 (2016): 11041-11049.
Millar, Biology statistics made simple using Excel. Sch. Sci. Rev. 23 (2001): 12 pages.
Millar, Neil. "Biology statistics made simple using Excel." School Science Review 83 (2001): 23-34.
Mortell, Kathleen H., Ross V. Weatherman, and Laura L. Kiessling. "Recognition specificity of neoglycopolymers prepared by ring-opening metathesis polymerization." Journal of the American Chemical Society 118.9 (1996): 22972298.
Mortell, Kathleen H., Marc Gingras, and Laura L. Kiessling. "Synthesis of cell agglutination inhibitors by aqueous ring-opening metathesis polymerization." Journal of the American Chemical Society 116.26 (1994): 12053-12054.
Murphy, John L., et al. "Adhesive performance of biomimetic adhesive-coated biologic scaffolds." Biomacromolecules 11.11 (2010): 2976-2984.
Muthukrishnan, Sharmila, et al. "Immobilized hyperbranched glycoacrylate films as bioactive supports." Macromolecular bioscience 6.8 (2006): 658-666.
Muthukrishnan, Sharmila, et al. "Synthesis and characterization of surface-grafted hyperbranched glycomethacrylates." Macromolecules 39.8 (2006): 2743-2750.
Narumi, Atsushi, et al. "Glycoconjugated polymer. 3. Synthesis and amphiphilic property of core-glycoconjugated star-shaped polystyrene." Macromolecules 35.3 (2002): 699-705.
Nasiri, Mohammadreza, and Theresa M. Reineke. "Sustainable glucose-based block copolymers exhibit elastomeric and adhesive behavior." Polymer Chemistry 7.33 (2016): 5233-5240.

Ninan, Lal, et al. "Adhesive strength of marine mussel extracts on porcine skin." Biomaterials 24.22 (2003): 4091-4099.
Nishiyama, Yuichi, et al. "Dismantlement behavior and strength of dismantlable adhesive including thermally expansive particles." International journal of adhesion and adhesives 23.5 (2003): 377-382.
North, Michael A., Chelsey A. Del Grosso, and Jonathan J. Wilker. "High strength underwater bonding with polymer mimics of mussel adhesive proteins." ACS applied materials & interfaces 9.8 (2017): 7866-7872.
Park, Joonyoung, et al. "Polydopamine-based simple and versatile surface modification of polymeric nano drug carriers." ACS nano 8.4 (2014): 3347-3356.
Park, Kinam. "Controlled drug delivery systems: past forward and future back." Journal of Controlled Release 190 (2014): 3-8.
Pearson, Samuel, Nathan Allen, and Martina H. Stenzel. "Core-shell particles with glycopolymer shell and polynucleoside core via RAFT: From micelles to rods." Journal of Polymer Science Part A: Polymer Chemistry 47.6 (2009): 1706-1723.
Pelliccioli, Anna Paola, and Jakob Wirz. "Photoremovable protecting groups: reaction mechanisms and applications." Photochemical & photobiological sciences 1.7 (2002): 441-458.
Peng, Xu, et al. "A zwitterionic gel electrolyte for efficient solid-state supercapacitors." Nature communications 7 (2016): 11782.
Perrini, Michela, et al. "A comparative investigation of mussel-mimetic sealants for fetal membrane repair." Journal of the mechanical behavior of biomedical materials 58 (2016): 57-64.
Ping, Jianfeng, et al. "Adhesive curing through low-voltage activation." Nature communications 6 (2015): 8050.
Pinto, Atahualpa, et al. "Chemically intractable no more: in vivo incorporation of "click"-ready fatty acids into poly-[(R)-3-hydroxyalkanoates] in *Escherichia coli*." ACS Macro Letters 5.2 (2016): 215-219.
Pramudya, Irawan, et al. "POSS-containing bioinspired adhesives with enhanced mechanical and optical properties for biomedical applications." Biomacromolecules 17.12 (2016): 3853-3861.
Pursifull, Nathan F., and Allen F. Morey. "Tissue glues and nonsuturing techniques" Current opinion in urology 17.6 (2007): 396-401.
Beauchamp, B. M. Evers, K. L. Mattox, In Sabiston Textbook of Surgery; Townsend, C. M., Ed.; Elsevier: Philadelphia, 2017, pp. 281-326.
Ramsubhag, Ron R., and Gregory B. Dudley. "Orthogonal dual-click diyne for CuAAC and/or SPAAC couplings." Organic & biomolecular chemistry 14.22 (2016): 5028-5031.
Rapi, Zsolt, et al. "Synthesis and characterization of biobased epoxy monomers derived from d-glucose." European Polymer Journal 67 (2015): 375-382.
Roy, Debashish, Jennifer N. Cambre, and Brent S. Sumerlin. "Sugar-responsive block copolymers by direct RAFT polymerization of unprotected boronic acid monomers." Chemical Communications 21 (2008): 2477-2479.
Ryu, Ji Hyun, et al. "Catechol-functionalized chitosan/pluronic hydrogels for tissue adhesives and hemostatic materials." Biomacromolecules 12.7 (2011): 2653-2659.
Ryu, Ji Hyun, Seonki Hong, and Haeshin Lee. "Bio-inspired adhesive catechol-conjugated chitosan for biomedical applications: A mini review." Acta biomaterialia 27 (2015): 101-115.
Scognamiglio, Francesca, et al. "Adhesive and sealant interfaces for general surgery applications." Journal of Biomedical Materials Research Part B: Applied Biomaterials 104.3 (2016): 626-639.
Sedó, Josep, et al. "Catechol-based biomimetic functional materials." Advanced Materials 25.5 (2013): 653-701.
Selvaraj, Vellaisamy, et al. "Cytotoxicity and genotoxicity caused by yttrium oxide nanoparticles in HEK293 cells." International journal of nanomedicine 9 (2014): 1379.
Seo, Sungbaek, et al. "Microphase behavior and enhanced wet-cohesion of synthetic copolyampholytes inspired by a mussel foot protein." Journal of the American Chemical Society 137.29 (2015): 9214-9217.
Serra, Laura, Josep Doméenech, and Nicholas A. Peppas. "Engineering design and molecular dynamics of mucoadhesive drug delivery systems as targeting agents." European journal of pharmaceutics and biopharmaceutics 71.3 (2009): 519-528.

(56) References Cited

PUBLICATIONS

Shan, Meng, et al. "A pH, glucose, and dopamine triple-responsive, self-healable adhesive hydrogel formed by phenylborate-catechol complexation." Polymer Chemistry 8.19 (2017): 2997-3005.

Shin, Jisoo, et al. "Tissue adhesive catechol-modified hyaluronic acid hydrogel for effective, minimally invasive cell therapy." Advanced Functional Materials 25.25 (2015): 3814-3824.

Sin, Mei-Chan, Sheng-Han Chen, and Yung Chang. "Hemocompatibility of zwitterionic interfaces and membranes." Polymer journal 46.8 (2014): 436-443.

Slegeris, Rimantas, Brian A. Ondrusek, and Hoyong Chung. "Catechol- and ketone-containing multifunctional bottlebrush polymers for oxime ligation and hydrogel formation." Polymer Chemistry 8.32 (2017): 4707-4715.

Sletten, Ellen M., and Carolyn R. Bertozzi. "From mechanism to mouse: a tale of two bioorthogonal reactions." Accounts of chemical research 44.9 (2011): 666-676.

Spain, Sebastian G., Luca Albertin, and Neil R. Cameron. "Facile in situ preparation of biologically active multivalent glyconanoparticles." Chemical Communications 40 (2006): 4198-4200.

Spotnitz, William D. "Fibrin sealant: the only approved hemostat, sealant, and adhesive—a laboratory and clinical perspective." ISRN surgery 2014 (2014), 203943.

Spotnitz, William D. "Hemostats, sealants, and adhesives: a practical guide for the surgeon." The American Surgeon 78.12 (2012): 1305-1321.

Spotnitz, William D., and Sandra Burks. "Hemostats, sealants, and adhesives: components of the surgical toolbox." Transfusion 48.7 (2008): 1502-1516.

Spotnitz, William D., and Sandra Burks. "State-of-the-art review: Hemostats, sealants, and adhesives II: Update as well as how and when to use the components of the surgical toolbox." Clinical and Applied Thrombosis/Hemostasis 16.5 (2010): 497-514.

Stuart, Martien A. Cohen, et al. "Emerging applications of stimuli-responsive polymer materials." Nature materials 9.2 (2010): 101.

Su, Jing, et al. "Catechol polymers for pH-responsive, targeted drug delivery to cancer cells." Journal of the American Chemical Society 133.31 (2011): 11850—11853.

Summerfield, Artur, François Meurens, and Meret E. Ricklin. "The immunology of the porcine skin and its value as a model for human skin." Molecular immunology 66.1 (2015): 14-21.

Sun, Peiyu, et al. "Facile preparation of mussel-inspired polyurethane hydrogel and its rapid curing behavior." ACS applied materials & interfaces 6.15 (2014): 12495-12504.

Sun, Xue-Long, et al. "Design and synthesis of biotin chain-terminated glycopolymers for surface glycoengineering." Journal of the American Chemical Society 124.25 (2002): 7258-7259.

Sundaram, Harihara S., et al. "One-step dip coating of zwitterionic sulfobetaine polymers on hydrophobic and hydrophilic surfaces." ACS applied materials & interfaces 6.9 (2014): 6664-6671.

Takigawa, Tomoko, and Yoko Endo. "Effects of glutaraldehyde exposure on human health." Journal of occupational health 48.2 (2006): 75-87.

Tibbitt, Mark W., Apr. M. Kloxin, and Kristi S. Anseth. "Modeling controlled photodegradation in optically thick hydrogels." Journal of Polymer Science Part A: Polymer Chemistry 51.9 (2013): 1899-1911.

Tibbitt, Mark W., et al. "Mechanical properties and degradation of chain and step-polymerized photodegradable hydrogels." Macromolecules 46.7 (2013): 2785-2792.

Tibbitt, Mark W., et al. "Synthesis and application of photodegradable microspheres for spatiotemporal control of protein delivery." Journal of biomedical materials research. Part A 100.7 (2012): 1647-1654.

Tillet, Guillaume, Bernard Boutevin, and Bruno Ameduri. "Chemical reactions of polymer crosslinking and post-crosslinking at room and medium temperature." Progress in Polymer Science 36.2 (2011): 191-217.

Ting, SR Simon, Andrew M. Gregory, and Martina H. Stenzel. "Polygalactose containing nanocages: the RAFT process for the synthesis of hollow sugar balls", Biomacromolecules 10.2 (2009): 342-352.

Ting, SR Simon, et al. "Controlled/living ab initio emulsion polymerization via a glucose RAFT stab: Degradable cross-linked glycoparticles for concanavalin A/Fim H Conjugations to cluster Escherichia coli bacteria." Macromolecules 43.12 (2010): 5211-5221.

Ting, SR Simon, Gaojian Chen, and Martina H. Stenzel. "Synthesis of glycopolymers and their multivalent recognitions with lectins." Polymer Chemistry 1.9 (2010): 1392-1412.

Tong, Rong, et al. "Smart chemistry in polymeric nanomedicine." Chemical Society Reviews 43.20 (2014): 6982-7012.

Tsutsumiuchi, Kaname, Keigo Aoi, and Masahiko Okada. "Synthesis of polyoxazoline-(glyco) peptide block copolymers by ring-opening polymerization of (sugar-substituted) α-amino acid N-carboxyanhydrides with polyoxazoline macroinitiators." Macromolecules 30.14 (1997): 4013-4017.

Tummatorn, Jumreang, et al. "Strain-Promoted Azide—Alkyne Cycloadditions of Benzocyclononynes." The Journal of organic chemistry 77.5 (2012): 2093-2097.

Uhlig, Nick, and Chao-Jun Li. "Alkynes as an eco-compatible "on-call" functionality orthogonal to biological conditions in water." Chemical Science 2.7 (2011): 1241-1249.

Vázquez-Dorbatt, Vimary, and Heather D. Maynard. "Biotinylated glycopolymers synthesized by atom transfer radical polymerization." Biomacromolecules 7.8 (2006): 2297-2302.

Von der Ehe, Christian, et al. "Immobilized glycopolymers: Synthesis, methods and applications." Progress in Polymer Science 57 (2016): 64-102.

Wang, Rui, et al. "A Biomimetic Mussel-Inspired ε-Poly-1-lysine Hydrogel with Robust Tissue-Anchor and Anti-Infection Capacity." Advanced Functional Materials 27.8 (2017): 1604894.

White, James D., and Jonathan J. Wilker. "Underwater bonding with charged polymer mimics of marine mussel adhesive proteins." Macromolecules 44.13 (2011): 5085-5088.

Xu, Jinke, et al. "Genipin-crosslinked catechol-chitosan mucoadhesive hydrogels for buccal drug delivery." Biomaterials 37 (2015): 395-404.

Xu, Ying, et al. "Mussel-Inspired Polyesters with Aliphatic Pendant Groups Demonstrate the Importance of Hydrophobicity in Underwater Adhesion." Advanced Materials Interfaces 4.22 (2017): 1700506.

Nishiyama and C. Sato, in Adhesion: Current Research and Applications, ed. W. Possart, Wiley-VCH, Weinheim, 2006, ch. 34, pp. 555-568.

Yilmaz, H. Gülşn, et al. "Kolokolik Anastomoz Güvenliğinde Fibrin Doku Yapiştriricinin Etkinligi." Ulusal Travmna ve Acil Cerrahi Dergisi 7.2 (2001): 87-90. English Abstract included.

Zhang, Hong, et al. "Catechol functionalized hyperbranched polymers as biomedical materials." Progress in Polymer Science 78 (2018): 47-55.

Zhang, Xuejiao, et al. "Micro-and nanogels with labile crosslinks—from synthesis to biomedical applications." Chemical Society Reviews 44.7 (2015): 1948-1973.

Zhao, Qiang, et al. "Underwater contact adhesion and microarchitecture in polyelectrolyte complexes actuated by solvent exchange." Nature materials 15.4 (2016): 407.

Zhao, Xuanhe, et al. "Active scaffolds for on-demand drug and cell delivery." Proceedings of the National Academy of Sciences 108.1 (2011): 67-72.

Zheng, Rui, et al. "Effect of adhesive characteristics on static strength of adhesive-bonded aluminum alloys." International Journal of Adhesion and Adhesives 57 (2015): 85-94.

Zhou, Hang, et al. "Photocleavage of the corona chains of rigid-rod block copolymer micelles." Macromolecules 48.7 (2015): 2254-2262.

Zhou, Jinjun, et al. "Adhesion properties of catechol-based biodegradable amino acid-based poly (ester urea) copolymers inspired from mussel proteins." Biomacromolecules 16.1 (2014): 266-274.

Zhu, Yicheng, et al. "The synthesis and aqueous solution properties of sulfobutylbetaine (co) polymers: comparison of synthetic routes and tuneable upper critical solution temperatures." Polymer Chemistry 6.31 (2015): 5705-5718.

(56) References Cited

PUBLICATIONS

Zosel, A. "Effect of cross-linking on tack and peel strength of polymers." The Journal of Adhesion 34.1-4 (1991): 201-209.

* cited by examiner

ZWITTERIONIC CROSSLINKED POLYMER-BASED ADHESIVES

BACKGROUND

Biomedical adhesive polymers are nonmetallic materials which possess the ability to join together two tissue surfaces by bonding. Tissues targeted by biomedical adhesives cover everything from hard tissues (bone, tooth, cartilage) to soft tissues (most other organs). The most extensively studied area of application of biomedical adhesives is the replacement of conventional wound closure methods such as sutures and staples (F. Scognamiglio, et al., *J. Biomed. Mater. Res., Part B* 2016, 104, 626-639; K. Park, *J. Controlled Release* 2014, 190, 3-8; W. D. Spotnitz. *Am. Surg.* 2012, 78, 1305-1321). In addition to wound closure, biomedical adhesives have also been applied as hemostatic agents, sealants, wound dressings, and drug delivery matrices (L. Serra, et al., *Eur. J. Pharm. Biopharm.* 2009, 71, 519-528; J. Xu, et al., *Biomaterials* 2015, 37, 395-404).

Conventional biomedical adhesives come in two major forms, the first being fully-synthetic adhesives including cyanoacrylate-based adhesives (e.g., Dermabond, Omnex, Histoacryl blue, Glubran 2, Surgiseal, Gluseal, Pattex, and Indermil) and poly(ethylene glycol) (PEG)-based adhesives. The second class of adhesives includes protein-based adhesives primarily containing fibrin (e.g., Tisseel, Crosseal, and Evicel), gelatin (e.g., GRF glue and Gluetiss), and albumin (e.g., BioGlue)(W. D. Spotnitz, *AORN J.* 2014, 100, 160-176; S. S. Kommu, et al., *Rev. Urol.* 2015, 17, 150-159; W. D. Spotnitz. *ISRN Surg.* 2014, 203943; S. P. Mandell, et al., *Expert Opin. Biol. Ther.* 2014, 14, 821-830; W. D. Spotnitz, et al., *Clin. Appl. Thromb./Hemostasis* 2010, 16, 497-514; W. D. Spotnitz, et al., *Transfusion* 2008, 48, 1502-1516; N. F. Pursifull, et al., *Curr. Opin. Neurol.* 2007, 17, 396-401). These current adhesives are widely applicable but suffer from a number of shortcomings. Cyanoacrylate adhesives, for example, are incompatible with internal soft tissue because of the stiffness of the resulting adhesive layer as well as the moderate amount of heat generated during the curing process. Protein-based adhesives which utilize rapid crosslinking action between serum and crosslinkers (stored separately in a dual-barreled syringe) offer certain advantages but suffer from poor temporal and spatial control during application. Additionally, the most common crosslinking agent, glutaraldehyde, may pose some safety concerns (T. Takigawa, et al., *J. Occup. Health* 2006, 48, 75-87). Therefore, the design of a biomedical adhesive to combat these shortcomings would be of high value to the surgical and greater medical community and there exists a strong need for new advanced functional materials in the field of biomedical adhesives, as well as in other fields. The compositions and methods disclosed herein address these.

Additionally, recent research has seen a trend of multifunctionality in biomedical adhesives with such functions as sensitivity toward external stimuli and drug delivery being combined with the traditional properties of a conventional polymer adhesive (B. T. Michal, et al., *ACS Appl. Mater. Interfaces,* 2016, 8, 11041-11049; M. A. C. Stuart, et al., *Nat. Mater.,* 2010, 9, 101-113; L. Serra, et al., *Eur. J. Pharm. Biopharm.,* 2009, 71, 519-528; T. Harper, et al., *ACS Appl. Mater. Interfaces,* 2017, 9, 1830-1839; Y. Jiao, et al., *Colloids Surf., B,* 2016, 140, 361-372). Stimulus-responsive adhesive polymers offer the ability to change their chemical structure upon receiving stimuli from the environment, often resulting in a significant change of bulk properties. Such stimuli include pH changes, light, changes in temperature, electricity, magnetic fields and mechanical forces (D. Kuckling, et al., in Polymer Science: A Comprehensive Reference, eds. K. Matyjaszewski and M. Möller, Elsevier, Amsterdam, 2012, vol. 8, pp. 377-413). Stimuli-responsive polymers are already used for a variety of applications including sensors, drug delivery, tissue engineering, and reconstructive polymer architectures. Recent advances in polymer synthesis and characterization has granted researchers the ability to precisely introduce functional groups within a macromolecular architecture, an advancement that functional polymers have leveraged to great effect. However, there are relatively few studies involving adhesive polymers containing multiple functionalities with the ability to respond to external stimuli, mainly because of the synthetic challenge still present in creating such polymers. What are thus needed are new stimuli-responsive multifunctional polymer adhesives and methods of making and using them. The compositions and methods disclosed herein also address these needs.

SUMMARY

In accordance with the purposes of the disclosed materials and methods, as embodied and broadly described herein, the disclosed subject matter, in one aspect, relates to compounds, compositions and methods of making and using compounds and compositions. In specific aspects, the disclosed subject matter relates to terpolymer adhesives comprising three different repeating domains: a catechol containing domain, a zwitterionic domain, and a crosslinking domain. In specific examples, the polymer can contain a 3,4-dihydroxy-L-phenylalanine (DOPA) segment which contains a catechol group, a poly(sulfobetaine methacrylate) (polySBMA, Polymer 5), and poly(ethylene glycol) dimethacrylate (PEGDMA) for light crosslinking. Alternatively, a photocleavable nitrobenzyloxycarbonyl containing crosslinker can be used. The disclosed polymers can be used as biomedical adhesives, such as to prevent leakage from the sutured intestinal tissue.

Additional advantages will be set forth in part in the description that follows, and in part will be obvious from the description, or may be learned by practice of the aspects described below. The advantages described below will be realized and attained by means of the elements and combinations particularly pointed out in the appended claims. It is to be understood that both the foregoing general description and the following detailed description are exemplary and explanatory only and are not restrictive.

BRIEF DESCRIPTION OF THE FIGURES

The accompanying figures, which are incorporated in and constitute a part of this specification, illustrate several aspects described below.

DETAILED DESCRIPTION

Figure 1:
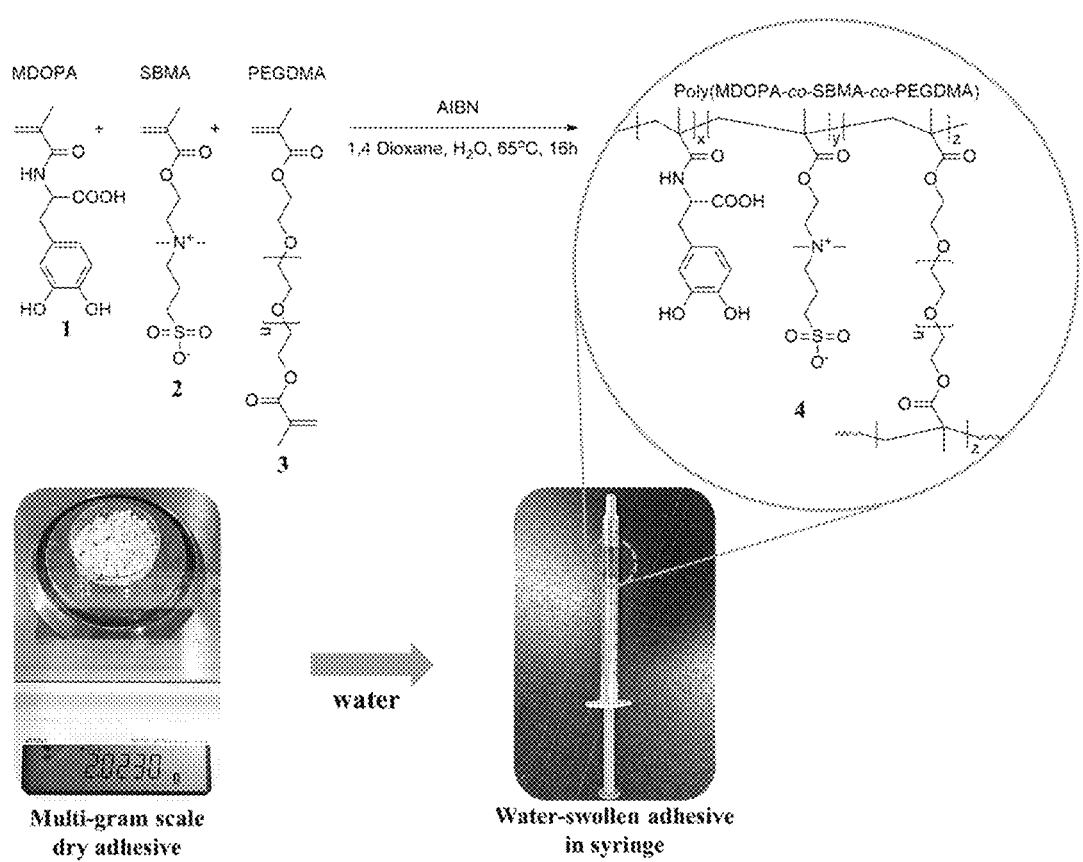
FIG. 1 shows the synthetic protocol for the thermally-initiated free radical polymerization resulting in the desired terpolymer 4. The terpolymer shown in the photos is poly (MDOPA$_{15}$-co-SBMA$_{85}$-co-PEGDMA$_{1.5}$).

The materials, compounds, compositions, and methods described herein may be understood more readily by reference to the following detailed description of specific aspects of the disclosed subject matter and the Examples included therein.

Before the present materials, compounds, compositions, and methods are disclosed and described, it is to be understood that the aspects described below are not limited to specific synthetic methods or specific reagents, as such may, of course, vary. It is also to be understood that the terminology used herein is for the purpose of describing particular aspects only and is not intended to be limiting.

Also, throughout this specification, various publications are referenced. The disclosures of these publications in their entireties are hereby incorporated by reference into this application in order to more fully describe the state of the art to which the disclosed matter pertains. The references disclosed are also individually and specifically incorporated by reference herein for the material contained in them that is discussed in the sentence in which the reference is relied upon.

General Definitions

In this specification and in the claims that follow, reference will be made to a number of terms, which shall be defined to have the following meanings:

Throughout the specification and claims the word "comprise" and other forms of the word, such as "comprising" and "comprises," means including but not limited to, and is not intended to exclude, for example, other additives, components, integers, or steps.

As used in the description and the appended claims, the singular forms "a," "an," and "the" include plural referents unless the context clearly dictates otherwise. Thus, for example, reference to "a composition" includes mixtures of two or more such compositions, reference to "an inhibitor" includes mixtures of two or more such inhibitors, and the like.

"Optional" or "optionally" means that the subsequently described event or circumstance can or cannot occur, and that the description includes instances where the event or circumstance occurs and instances where it does not.

Notwithstanding that the numerical ranges and parameters setting forth the broad scope of the disclosure are approximations, the numerical values set forth in the specific examples are reported as precisely as possible. Any numerical value, however, inherently contain certain errors necessarily resulting from the standard deviation found in their respective testing measurements. Furthermore, when numerical ranges of varying scope are set forth herein, it is contemplated that any combination of these values inclusive of the recited values may be used. Further, ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. Unless stated otherwise, the term "about" means within 5% (e.g., within 2% or 1%) of the particular value modified by the term "about."

It is understood that throughout this specification the identifiers "first" and "second" are used solely to aid in distinguishing the various components and steps of the disclosed subject matter. The identifiers "first" and "second" are not intended to imply any particular order, amount, preference, or importance to the components or steps modified by these terms.

As used herein, the term "composition" is intended to encompass a product comprising the specified ingredients in the specified amounts, as well as any product which results, directly or indirectly, from combination of the specified ingredients in the specified amounts.

The term "catechol," as used herein, refers to 1,2-dihydroxybenzene moiety.

The term "domain" as used herein refer to a region of a polymer that has a common structure or property. A domain can be pendant to a polymer backbone, e.g., a grafted domain, or within the polymer backbone, e.g., a polymer segment. A domain can also refer to monomer residues within a polymer, whether randomly distributed or in blocks. There is no limit to the size of the domain in relation to the polymer itself, thus a domain can comprise as little as two monomers or as much as nearly 100% of the polymer.

The term "polyzwitterions" as used refer to a polymer or domain where a repeating unit of the polymer chain contains a zwitterionic moiety. Polyzwitterions are also known as polybetaines. The cationic and anionic groups are both part of the same repeating unit, which means a polyzwitterion has the same number of cationic groups and anionic groups. Also, polyzwitterions have the cationic group and anionic group as part of a repeating unit.

The terms "zwitterion" and "zwitterionic compound" as used herein refers to compounds in which a neutral molecule of the compound has a unit positive and unit negative electrical charge at different locations within the molecule. Such compounds are a type of dipolar compounds and are also sometimes referred to as "inner salts."

References in the specification and concluding claims to parts by weight of a particular element or component in a composition denotes the weight relationship between the element or component and any other elements or components in the composition or article for which a part by weight is expressed. Thus, in a mixture containing 2 parts by weight of component X and 5 parts by weight component Y, X and Y are present at a weight ratio of 2:5, and are present in such ratio regardless of whether additional components are contained in the mixture.

A weight percent (wt. %) of a component, unless specifically stated to the contrary, is based on the total weight of the formulation or composition in which the component is included.

Reference will now be made in detail to specific aspects of the disclosed materials, compounds, compositions, articles, and methods, examples of which are illustrated in the accompanying Examples and Figures.

Compositions

Disclosed herein is are terpolymer adhesives. The disclosed adhesives comprise a catechol domain, a zwitterionic domain, and a crosslinking domain. In specific embodiments, the crosslinking domain can be a photoreactive crosslinking domain.

Catechol Containing Domain

Adhesives containing catechol moieties have gained extensive interest in polymer science due to their strong wet adhesion properties, opening the door to their biological and biomedical applications. Catechol is a major structural component in 3,4-dihydroxy-L-phenylalanine (DOPA), a modified amino acid utilized by marine organisms such as mussels and sandcastle worms. The catechol group in DOPA is an essential contributor to the strong adhesion properties of plaque proteins (B. P. Lee, et al., *Annu. Rev. Mater. Res.*, 2011, 41, 99-132; J. Sedó, et al., *Adv. Mater.*, 2013, 25, 653-701). Although it is known that the catechol group generally strengthens the interfacial adhesion properties of the synthetic polymers, catechol alone does not always result in superior adhesion. Rather, the catechol functionality must be integrated within well-defined polymers which possess optimum viscoelastic properties, cohesion bond formation (crosslinking) properties, water compatibility, and mechanical properties (E. Faure, et al., *Prog. Polym. Sci.*, 2013, 38, 236-270; H. Chung et al., *Macromolecules*, 2012, 45, 9666-9673; P. Glass, et al., *Langmuir*, 2010, 26, 17357-17362; H. Chung, et al., *Biomacromolecules*, 2011, 12, 342-347). Catechol can work synergistically with these other components to improve overall adhesive performance only when incorporated into well-understood and well-defined polymer structures. Catechol-containing polymers have been used for various biomedical purposes such as drug carriers, biomedical glues, and actuators (I. Pramudya, et al., *Biomacromolecules*, 2016, 17, 3853-3861; K. Kim, et al., *Biomaterials*, 2015, 52, 161-170; J. Xu, et al., *Biomaterials*, 2015, 37, 395-404; J. L. Murphy, et al., *Biomacromolecules*, 2010, 11, 2976-2984; B. P. Lee, et al., *Adv. Mater.*, 2014, 26, 3415-3419).

The disclosed polymer adhesives have a domain comprising a catechol group. For example, the disclosed polymer adhesives can comprise a catechol domain having repeating units derived from the following monomer.

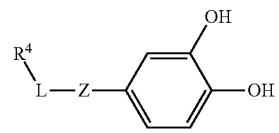

where Z is branched or straight chain alkyl, heteroalkyl, cycloalkyl, cycloheteroalkyl, aryl, or heteroaryl; L is a linker such as a bond, NH, O, C(O), C(O)O, or NH(CO); and $R^4$ is a polymerization group.

The term "polymerization group" as used herein refer to a functional group that permits polymerization of the monomer with itself to form a homopolymer or together with different monomers to form a copolymer. Depending on the type of polymerization methods employed, the polymerization group can be selected from alkene, alkyne, epoxide, lactone, amine, hydroxyl, isocyanate, carboxylic acid, anhydride, silane, halide, aldehyde, and carbodiimide. In certain aspects the polymerization group is an alkene.

In these monomers, Z can have a length of from 1 to 12 atoms, e.g., from 1, 2, 3, 4, 5, 6, 7, 8, 9, 10, 11, or 12 atoms, where any of these values can form an upper or lower endpoint of a range.

In specific examples, the catechol domain can comprise the monomer derived from dopamine as shown below.

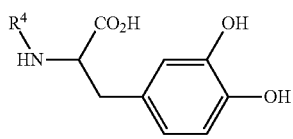

The catechol domain can be "internal" in reference to the polymer backbone. Such "internal" repeating units are distinguished from a material that is found at the end of a polymer chain since such a moiety would only be bonded to the polymer chain at one location.

The catechol domain can be prepared by radical polymerization of catechol containing monomers having unsaturated moieties substituted at position Z in the monomer shown above. In other examples zwitterionic monomers where an unsaturated moiety is attached to the amine group can be used in a radical polymerization. Examples of such monomers are shown below.

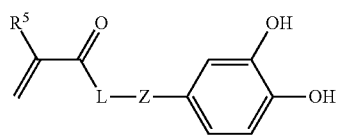

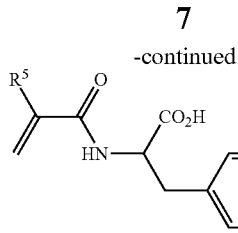

where Z and L are as defined before and $R^5$ are independently chosen from heteroalkyl, cycloalkyl, cycloheteroalkyl, aryl, or heteroaryl. In specific examples, $R^5$ is H or $CH_3$.

In specific examples, the catechol domain can comprise from about 1 to about 50 mole % of the polymer, sometimes from about 5 to 25 mole %, and other times from about 10 to 20 mole %, and still other times about 15 mole %. The catechol domain can have a molecular weight of from about 160 daltons to about 10,000 daltons, and sometimes from about 200 daltons to about 2,000 daltons. In some embodiments, the molecular weight of the soft segments can be from about 200 daltons to about 10,000,000 daltons, and sometimes from about 500 daltons to about 5,000 daltons, and sometimes from about 500 daltons to about 2,000 daltons.

Zwitterionic Domain

Another requirement of an effective polymeric adhesive is a suitable base polymer for desirable biomedical applications. Zwitterionic polymers can improve the adhesion strength of polymer adhesives via ionic interactions (X. Peng, et al., *Nat. Commun.*, 2016, 7, 11782). Additionally, the charges in the zwitterionic polymer backbone serve to increase the oxidation stability of catechol through electrophilic shielding in a coacervate environment (S. Seo, et al., *J. Am. Chem. Soc.*, 2015, 137, 9214-9217; B. K. Ahn, et al., *Nat. Commun.*, 2015, 6, 8663). Further, in order to form a strong bond to human tissue under physiological conditions, the polymer adhesive should be highly hydrophilic (G. P. Maier, et al., *Science,* 2015, 349, 628-632; R. Zheng, et al., *Int. J. Adhes. Adhes.*, 2015, 57, 85-94; S. A. Mian, et al., *Theor. Chem. Acc.*, 2011, 130, 333-339; S. A. Mian, et al., *J. Phys. Chem. C,* 2010, 114, 20793-20800). Zwitterionic polymers have a high level of hydrophilicity due to ionic attraction to water originating from the charge sepearated nature of their chemical structure. In addition, zwitterionic polymers demonstrate stability over a wide pH range in aqueous solution (A. Callow et al., *Nat. Commun.*, 2011, 2, 244; Z. Cao, L. et al., *Langmuir,* 2012, 28, 11625-11632; R. Lalani et al., *Biomacromolecules,* 2012, 13, 1853-1863; H. S. Sundaram, et al., *ACS Appl. Mater. Interfaces,* 2014, 6, 6664-6671). Thus, zwitterionic polymers have gained substantial attention as next-generation biomaterials that can replace conventionally used PEG adhesives because of their comparatively superior long-term stability in complex biological systems (M.-C. Sin, et al., *Langmuir,* 2008, 24, 5453-5458).

In the disclosed polymer adhesives, the zwitterionic domain can be a polyzwitterion. Polyzwitterions can have a variety of repeating units, which are illustrated as i) through vii) below, where n is some integer from 2 to 1000:

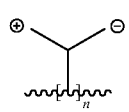

i)

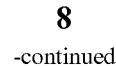

ii)

iii)

iv)

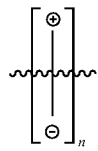

v)

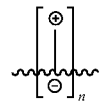

vi)

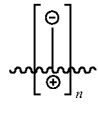

vii)

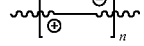

In structures i) through iv) the zwitterionic unit is connected to the backbone chain (⁓⁓⁓) and the charges are on side-groups that are pendant to the chain. In structures v) through vii) the zwitterionic unit is such that one or both charges is on the chain itself.

Examples of suitable zwitterionic monomers that can be used to produce a polyzwitterion of any of structures i) through vii) include:

ammoniophosphates (phosphobetaines or lecithin analogues), ammoniophosphonates (phosphonobetaines), or ammoniophosphinates (phosphinobetaines), respectively having the structures

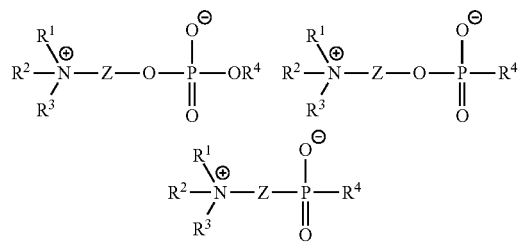

where Z is branched or straight chain alkyl, heteroalkyl, cycloalkyl, cycloheteroalkyl, aryl, or heteroaryl; $R^1$ is H, alkyl, heteroalkyl, cycloalkyl, heterocycloalkyl, aryl, or heteroaryl; and $R^2$, $R^3$, and $R^4$ are independently chosen from alkyl, heteroalkyl, cycloalkyl, heterocycloalkyl, aryl, or heteroaryl; wherein one or more of $R^1$, $R^2$, $R^3$, $R^4$, and Z are substituted with a polymerization group; or ammoniosulfonates (sulfobetaines), ammoniosulfates, respectively having the structures:

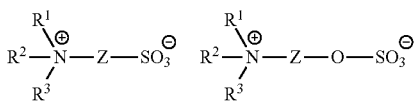

where Z is branched or straight chain alkyl, heteroalkyl, cycloalkyl, cycloheteroalkyl, aryl, or heteroaryl; $R^1$ is H, alkyl, heteroalkyl, cycloalkyl, heterocycloalkyl, aryl, or heteroaryl; and $R^2$ and $R^3$, are independently chosen from alkyl, heteroalkyl, cycloalkyl, heterocycloalkyl, aryl, or heteroaryl; wherein one or more of $R^1$, $R^2$, $R^3$, and Z are substituted with a polymerization group.

In each of these monomers Z can have a length of from 1 to 12 atoms, e.g., from 1, 2, 3, 4, 5, 6, 7, 8, 9, 10, 11, or 12 atoms, where any of these values can form an upper or lower endpoint of a range.

The zwitterionic domain can be "internal" in reference to the polymer backbone. Such "internal" repeating units are distinguished from a material that is found at the end of a polymer chain since such a moiety would only be bonded to the polymer chain at one location.

The zwitterionic domain can be prepared by radical polymerization of zwitterionic monomers having unsaturated moieties substituted at position Z in the monomers shown above. In other examples zwitterionic monomers where an unsaturated moiety is attached to the ammonium group can be used in a radical polymerization. Examples of such monomers are shown below:

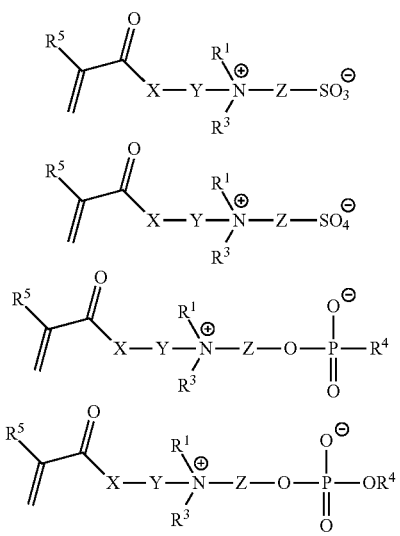

where X is O, NH, or $NR^4$, Y and Z are, independently, branched or straight chain alkyl, heteroalkyl, cycloalkyl, cycloheteroalkyl, aryl, or heteroaryl, and of which can be optionally substituted with OH, halogen, or alkoxyl; $R^1$ is H, alkyl, heteroalkyl, cycloalkyl, cycloheteroalkyl, aryl, or heteroaryl; and $R^3$ and $R^5$ are independently chosen from heteroalkyl, cycloalkyl, cycloheteroalkyl, aryl, or heteroaryl. In specific examples, $R^5$ is H or $CH_3$. In other examples, X is O. In still other examples, X is NH or $NCH_3$. In specific examples Y is $C_1$-$C_4$ alkyl. In other examples Z is $C_1$-$C_4$ alkyl.

Additional examples of suitable zwitterionic monomers include N-(2-methacryloyloxy)ethyl-N,N-dimethylammonio propanesulfonate, N-(3-methacryloylimino)propyl-N,N-dimethylammonio propanesulfonate, 2-(methacryloyloxy)ethylphosphatidylcholine, and 3-(2'-vinyl-pyridinio) propanesulfonate.

In specific examples, the zwitterionic domain can comprise from 50 to about 99 mole % of the polymer, sometimes from about 60 to 98 mole %, sometimes from 70 to 97 mole %, sometimes from about 75 to 95 mole %, and other times from about 80 to 90 mole %, and still other times about 85 mole % of the polymer. The zwitterionic domain can have a molecular weight of from about 160 daltons to about 10,000 daltons, and sometimes from about 200 daltons to about 2,000 daltons. In some embodiments, the molecular weight of the soft segments can be from about 200 daltons to about 10,000,000 daltons, and sometimes from about 500 daltons to about 5,000 daltons, and sometimes from about 500 daltons to about 2,000 daltons.

In specific examples, the molar ratio of the catechol domain to the zwitterionic domain can be about 1 to about 99, about 5 to about 95, about 10 to about 90, or about 15 to about 85.

Here a zwitterionic polymer, such as poly(sulfobetaine methacrylate) (polySBMA), can be used as a base polymer, occupying that 85 mol % of the entire terpolymer adhesive structure. The described zwitterionic polymer is highly applicable to biomedical applications because of the high degree of hydrophilicity via ionic attraction to water and high biocompatibility (A. J. Keefe, et al., *Nat. Chem.* 2011, 4, 59; S. Chen, et al., *J. Am. Chem. Soc.* 2005, 127, 14473-14478; A. B. Lowe, et al., *Chem. Rev.* 2002, 102, 4177-4190). Additionally, the balanced charge (equal number of cationic and anionic charges) in individual repeating unit acts as a buffer, providing stability over a wide range of pH in aqueous biological solutions. Finally, the methacrylate moiety of the zwitterionic monomer allows for convenient radical polymerization in the preparation of desirable polymeric adhesives.

Crosslinking Domain

To achieve strong adhesion properties, adhesives must interact quickly with targeted surfaces. During the contact process, it is essential that the adhesive be highly flexible because most biological surfaces are not uniformly smooth. The more flexible that the adhesive is, the greater contact will be generated by flowing into all areas. In addition to this fast wetting process, an adhesive should efficiently resist debonding in order to maintain adhesion. Generally, flexible adhesive polymers can easily lose their original formation by the application of external force, or debonding. In polymer adhesives, resistance to debonding is commonly enhanced by crosslinking. In other words, crosslinking can enhance the overall adhesion properties of polymeric adhesives (A. N. Gent, *Langmuir* 1996, 12, 4492-4496; A. Zosel, *J. Adhes.* 1991, 34, 201-209). Excessively crosslinked polymers, however, may lose their flexibility, leading to poor initial interfacial contact between the adhesive and the target surface. For these reasons, finding an ideal degree of crosslinking can be an important step in the design of effective polymer adhesives (M. Kim, et al., *Polym. Chem.* 2017, 8, 6300-6308; T. Harper, et al., *ACS Appl. Mater. Interfaces* 2017, 9, 1830-1839).

The crosslinking domain of the disclosed polymer adhesives can be formed from a crosslinking monomer. The crosslinking monomer can have reactive groups that are available for bond formation; that is, the crosslinking monomer can be reacted with the reactive groups (e.g., $R^1$-$R^5$ of the catechol and/or zwitterionic monomer) of the polymer. Examples of reactive groups on a suitable crosslinking monomer include nucleophilic groups or electrophilic groups. The reactive groups of the crosslinking monomer can be complementary to the reactive groups of the catechol and/or zwitterionic domains. For example, the reactive groups of the catechol and/or zwitterionic domains can comprise nucleophilic reactive groups and the crosslinking monomer can comprise electrophilic reactive groups. Alternatively, the reactive groups of the catechol and/or zwitterionic domains can comprise electrophilic reactive groups and the crosslinking monomer can comprise nucleophilic reactive groups. Alternatively, the reactive groups of the catechol and/or zwitterionic domains can comprise radical polymerizable groups and the crosslinking monomer can comprise radical polymerizable groups.

In some examples, the crosslinking monomer can comprise 2 or more reactive groups (e.g., 3 or more, 4 or more, or 5 or more). In some examples the crosslinking monomer can comprise 6 or less reactive groups (e.g., 5 or less, 4 or less, or 3 or less). The number of reactive groups of the crosslinking monomer can range from any of the minimum values described above to any of the maximum values described above, for example from 2 to 6 (e.g., from 2 to 4, from 4 to 6, from 3 to 5, from 2 to 3, from 3 to 4, from 4 to 5, or from 5 to 6).

The amount of crosslinking monomer used can be 0.05 mole % or more based on the total amount of the monomers to be polymerized (e.g., 0.1% or more, 0.2% or more, 0.3% or more, 0.4% or more, 0.5% or more, 0.6% or more, 0.7% or more, 0.8% or more, 0.9% or more, 1% or more, 1.1% or more, 1.2% or more, 1.3% or more, 1.4% or more, 1.5% or more, 1.6% or more, 1.7% or more, 1.8% or more, 1.9% or more, 2% or more, 2.1% or more, 2.2% or more, 2.3% or more, 2.4% or more, 2.5% or more, 2.6% or more, 2.7% or more, 2.8% or more, or 3% or more). In some examples, the amount of crosslinking monomer used can be 4 mole % or less based on the total amount of the monomers to be polymerized (e.g., 3.9% or less, 3.8% or less, 3.7% or less, 3.6% or less, 3.5% or less, 3.4% or less, 3.3% or less, 3.2% or less, 3.1% or less, 3% or less, 2.9% or less, 2.8% or less, 2.7% or less, 2.6% or less, 2.5% or less, 2.4% or less, 2.3% or less, 2.2% or less, 2.1% or less, or 2% or less). The amount of crosslinking agent used can range from any of the minimum values described above to any of the maximum values described above. For example, the amount of crosslinking agent used can be from 0.05% to 2% based on the total amount of monomers to be polymerized (e.g., from 0.05% to 1%, from 1% to 2%, from 1% to 3.5%, from 0.5% to 1%, from 1% to 1.5%, from 1.5% to 2%, or from 1.5% to 2.5%). In specific examples, the amount of crosslinking monomer is less than 3.5 mole %.

Examples of suitable crosslinking monomers that can be used to form the crosslinking domain are those with the following structure.

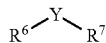

where Y is a linking moiety of from 1 to 1,000,000 atoms; and $R^6$ and $R^7$ are independently polymerization groups, as defined herein.

In specific examples, the crosslinking moiety can have the following structure,

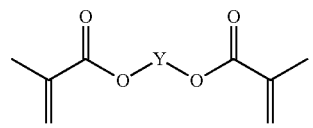

The linking moiety Y can in specific examples be a $C_2$-$C_6$ branched or straight-chain alkyl, wherein one or more of the carbon atoms is substituted with oxygen (e.g., an ether) or an amino group. For example, suitable examples of Y can include, but are not limited to, a methoxymethyl, methoxyethyl, methoxypropyl, methoxybutyl, ethoxymethyl, ethoxyethyl, ethoxypropyl, propoxymethyl, propoxyethyl, methylaminomethyl, methylaminoethyl, methylaminopropyl, methylaminobutyl, ethylaminomethyl, ethylaminoethyl, ethylaminopropyl, propylaminomethyl, propylaminoethyl, methoxymethoxymethyl, ethoxymethoxymethyl, methoxyethoxymethyl, methoxymethoxyethyl, and the like.

In specific examples, the linking moiety Y can be a polyalkoxyl chain. For example, the linking moiety Y can be a polyethyleneoxide or polypropyleneoxide segment from 50 to 5,000,000 daltons. In a specific example, the crosslinking monomer can have the formula where n is from 2 to 500,000.

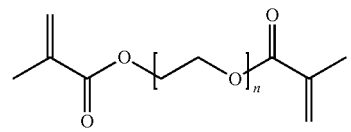

Photoreactive Crosslinking Domain

In specific examples, the crosslinking domain can be formed from a stimuli responsive crosslinking monomer. For example, crosslinking monomers that are sensitive, e.g., labile, in response to stimuli such as acid, base, heat, or light can be used. In specific examples, the crosslinking monomer can be sensitive to light, e.g., UV, IR, and/or visible light. In some specific examples, the crosslinking monomer can have the structure as detailed above where Y is a stimuli responsive moiety, e.g., a photolabile moiety. A specific example of a suitable photolabile moiety is nitrobenzene. A specific example of a suitable photoreactive crosslinking monomer is 2-nitro-1,3-benzenedimethanol dimethacrylate (NBDM).

Specific examples of terpolymer adhesives disclosed herein are poly(N-methacryloyl-3,4-dihydroxyl-L-phenylalanine-co-sulfobetaine methacrylate-co-poly(ethylene glycol) dimethacrylate) (poly(MDOPA-co-SBMA-co-PEGDMA) and poly(N-methacryloyl-3,4-dihydroxyl-L-phenylalanine-co-sulfobetaine methacrylate-co-2-nitro-1,3-benzenedimethanol dimethacrylate), poly(MDOPA-co-SBMA-co-NBDM).

Methods of Making

Disclosed herein are synthetic routes toward polymers possessing multiple functional groups within a single polymer structure, providing advanced functionalities such as photosensitivity, hydrophilicity, and strong wet adhesion properties. Among the various stimuli leveraged by stimuli-responsive polymers, light offers convenience in terms of spatial and temporal control. While a number of functional groups have been used for photolysis (e.g. 2-nitrobenzyl, coumarin-4-yl-methyl, p-hydroxyphenacyl, and 7-nitroindoline derivatives) (R. Tong, et al., Chem. Soc. Rev., 2014, 43, 6982-7012) the 2-nitrobenzyl functionality is regarded as one of the most important and useful photocleavable groups owing to its relatively simple synthesis, high yielding photocleavage, known mechanism of photocleavage, and biocompatibility before and after photodegradation (X. Zhang, et al., *Chem. Soc. Rev.*, 2015, 44, 1948-1973; C. M. Kirschner, et al., *Adv. Healthcare Mater.*, 2014, 3, 649-657).

Methods of Use

A variety of medical applications have been tested to utilize their strong wet-adhesion properties for internal organs. For example, Cha et al. presented a non-invasive method for the repair of urinary fistulas using a bioinspired adhesive comprising DOPA-containing recombinant protein and hyaluronic acid (HA) (H. J. Kim, et al., *Biomaterials* 2015, 72, 104-111; D. S. Hwang, et al., *Biomaterials* 2007, 28, 3560-3568). Other analogue adhesives of the HA and DOPA containing recombinant proteins were developed for orthopedic reconstruction (S. Lim, et al., *Biomaterials* 2010, 31, 3715-3722; H. J. Kim, et al., *Adv. Healthcare Mater.* 2016, 5, 3191-3202) and skin tissue adhesion (S. Han, et al., *ACS Nano* 2017, 11, 9979-9988). Messersmith, et al. developed PEG-based DOPA containing adhesives for the treatment of fetal membrane rupture (M. Perrini, et al., *J. Mech. Behav. Biomed. Mater.* 2016, 58, 57-64; G. Bilic, et al., *Am. J. Obstet. Gynecol.* 2010, 202, 85.e81-85.e89; A. Kivelio, et al., *Eur. J. Obstet. Gynecol. Reprod. Biol.* 2013, 171, 240-245) and islet transplantation (C. E. Brubaker, et al., *Biomaterials* 2010, 31, 420-427). Citrate-based bioinspired adhesives have been developed and used for antibacterial and antifungal purposes by Yang et. al. (*Biomaterials* 2017, 112, 275-286). In addition, various DOPA containing biomedical adhesives have been developed for adhesion to liver and heart tissue (J. Shin, et al., *Adv. Funct. Mater.* 2015, 25, 3814-3824), cancer drug delivery (J. Su, et al., *J. Am. Chem. Soc.* 2011, 133, 11850-11853; K. C. Black, et al., *Nanomedicine* 2013, 8, 17-28), wound dressing (R. Wang, et al., *Adv. Funct. Mater.* 2017, 27), hemostasis (D. Lu, H et al., *ACS Appl. Mater. Interfaces* 2017, 9, 16756-16766), and degradable surgical adhesives (V. Bhagat, et al., *Biomacromolecules* 2017, 18, 3009-3039).

Disclosed herein is a DOPA containing bioinspired adhesive that can be used to provide a water-proof sealing for a variety of indications. For example, the disclosed adhesives can be used to seal intestinal anastomoses and prevent potentially lethal anastomotic leakage. Intestinal anastomosis is a surgical procedure involving the resection and reconnection of intestinal segments. Intestinal anastomosis is performed for many reasons including the removal of intestinal tumors. Sutures and other perforating methods are the most common way to reconnect intestinal soft tissue post resection (H. Yilmaz, et al., *Travma Acil Cerrahi Derg.* 2001, 7, 87-90). However, in addition to the risk of infection and persisting pain associated with the use of internal sutures, suturing carries a potential risk of anastomotic leakage, or a leakage of the intestinal contents through anastomotic defective sites into the peritoneal cavity. The consequences of anastomotic leakage are varied, but it can be harmful and potentially deadly to the patient (P. Matthiessen, et al., *Ann. Surg.* 2007, 246, 207-214). Among the many factors influencing the rate of anastomotic leakage, the very first step of leakage prevention would be a complete physical sealing of the sutured or stapled anastomotic sites.

EXAMPLES

The following examples are set forth below to illustrate the methods and results according to the disclosed subject matter. These examples are not intended to be inclusive of all aspects of the subject matter disclosed herein, but rather to illustrate representative methods and results. These examples are not intended to exclude equivalents and variations of the present invention, which are apparent to one skilled in the art.

All reagents were purchased from Sigma-Aldrich Co. and TCI America and used without further purification unless otherwise stated. The average molecular weight of PEGDMA (purchased from Sigma-Aldrich) used as crosslinker is 750 g mol$^{-1}$. MDOPA 1 was synthesized and characterized as previously reported by I. Pramudya, et al., *Biomacromolecules* 2016, 17, 3853-3861. Porcine skin was purchased from a local grocery store. Porcine intestine was donated from a local slaughter house. Florida State University Animal Care and Use Committee (ACUC) protocol was not considered because there were no procedures involving live animals. Porcine skin was purchased from a local grocery store and porcine intestine was donated from a local slaughter house.

Example 1: Crosslinked Zwitterionic Polymers

Synthesis of Poly(MDOPA-co-SBMA-co-PEGDMA) (4)

MDOPA was prepared by treatment of L-DOPA with methacryloyl chloride in an aqueous borax solution. The other two acrylate monomers, SBMA (2) and PEGDMA (3), are commercially available. Terpolymer 4 was prepared by thermally-initiated free radical polymerization of MODPA 1, SBMA 2, and PEGDMA crosslinker 3 as shown in FIG. 1. The effect of the DOPA molar ratio on bulk adhesion properties has been previously reported in a thorough and systematic fashion (M. A. North, et al., *ACS Appl. Mater. Interfaces* 2017, 9, 7866-7872; C. R. Matos-Pérez, et al., *J. Am. Chem. Soc.* 2012, 134, 9498-9505). Here, a fixed 15:85 feed mole ratio of MDOPA to SBMA was used to test adhesion property of synthesized terpolymer.

Specifically, MDOPA 1 (0.94 g, 3.56 mmol, 0.15 equiv.), SBMA 2 (5.63 g, 20.14 mmol, 0.85 equiv.), PEGDMA 3 (ranging from 0.27 g to 0.62 g), and 2,2'-Azobis(2-methylpropionitrile) (radical initiator, 0.12 g, 0.71 mmol, 0.03 equiv.) were mixed in DI water/1,4 dioxane co-solvent (75.00 mL; the volume ratios between 1,4 dioxane and DI water is 1:1). Herein, the PEGDMA amounts were varied on desired crosslinking: 1.5% (0.27 g, 0.36 mmol), 2.0% (0.36 g, 0.48 mmol), 2.5% (0.45 g, 0.60 mmol), and 3.5% (0.62 g, 0.83 mmol). The mixture was degassed for 15 min by using dry nitrogen gas and then was stirred for 16h at 65° C., giving rise to a terpolymer 4. After the polymerization, impurities were removed by performing dialysis in DI water for 24h using a regenerated cellulose membrane (MWCO: 1 kD, Spectra/Por). After that, dry powder of 4 (1.10 g, 77%) was acquired by removing water using lyophilized. The synthetic procedure of homopolymer, polySBMA 5, copolymer, poly(MDOPA-co-SBMA) 6, and crosslinked zwitterionic polymer without MDOPA, poly(SBMA-co-PEGDMA) 7, were identical to that of the 4 except type of monomers.

Figure 2:
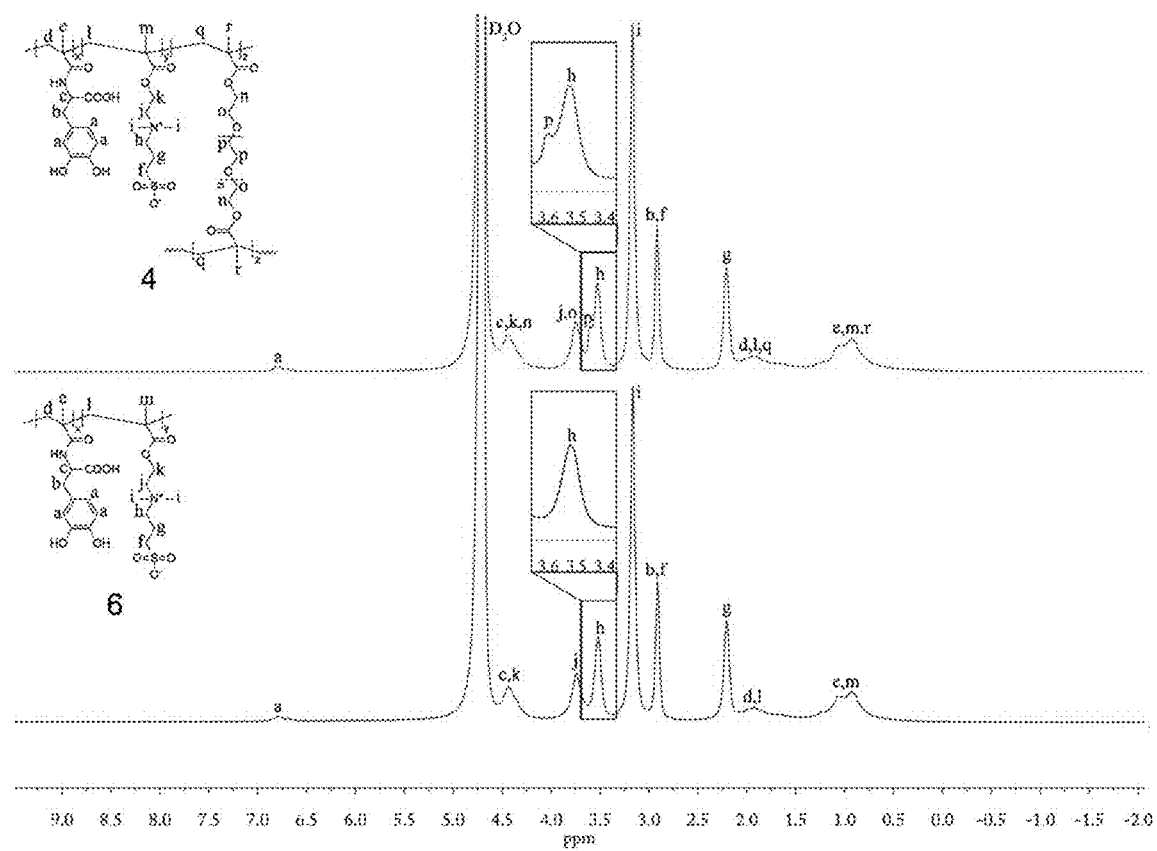
FIG. 2 shows $^1$H NMR spectra for terpolymer 4 and poly(SBMA-co-MDOPA) 6. The repeating unit ratio between SBMA and MDOPA in the copolymer 6 is 86:14.

The chemical structure of 4, 5, 6, and 7 were analyzed by $^1$H NMR (600 MHz, D$_2$O) spectroscopy. The $^1$H NMR spectra of 4 and 6 is shown in FIG. 2. To acquire $^1$H NMR spectrum of each polymer (4 (poly(MODPA$_{15}$-co-SBMA$_{85}$-co-PEGDMA$_{2.5}$), 5, and 6), the polymer (25 mg) was first dissolved in D$_2$O (0.5 mL). Then, 1.0 M NaCl solution (80 μL) was added to polymer solution for increasing polymer solubility (J. D. Delgado, et al., *Macromolecules* 2017, 50, 4454-4464; Y. Zhu, et al., *Polym. Chem.* 2015, 6, 5705-5718), giving rise to clear polymer solution (5 and 6, respectively). Although the resulting lightly crosslinked terpolymer 4 (poly(MODPA$_{15}$-co-SBMA$_{85}$-co-PEGDMA$_{2.5}$) solution in D$_2$O was slightly turbid due to light crosslinking, resulting terpolymer solution was sufficient to acquire adequate $^1$H NMR spectrum. The acquired spectrum of terpolymer clearly presented characteristic resonances of monomer moieties as previously reported in the literature for the successful structure determination of similar crosslinked zwitterionic polymers (J. Chang, et al., *J. Mater. Chem. B* 2015, 3, 1097-1105).

The spectrum of polymer 5 shows the distinct broad resonances attributed to MDOPA (peak at 6.79 ppm, FIG. 2, bottom), as well as those attributed to SBMA (resonances g, i, h, and j at 2.19, 3.16, 3.51, and 3.74 ppm, respectively). This analysis confirms the successful synthesis of poly(MODPA-co-SBMA) while peak integration indicates a repeating unit ratio of 86:14 of SBMA to MDOPA. The proton spectrum of 4 shows additional peaks, with a broad resonance at 3.60 ppm which is attributed to crosslinker 3, confirming the successful preparation of poly(MDOPA-co-SBMA-co-PEGDMA). $^1$H NMR spectra in FIG. 2 shows that the synthesized polymers have well-defined chemical structures with highly purity and reproducibility over different batches.

The amount of crosslinker 3 can strengthen the overall adhesion properties of the polymer; though too much can result in unfavorable mechanical properties. To that end, several variations of lightly crosslinked terpolymer 4 were created, with crosslinker feed amounts of 1.5, 2, 2.5, and 3.5 mol %. Herein, the crosslinker mol % is determined compared to the overall molarity of poly(SBMA-co-MDOPA). For instance, the mole ratio of 2.5% crosslinked terpolymer has a mole ratio of 15:85:2.5 for MDOPA:SBMA:PEGDMA. Control samples of homo-zwitterionic polymer, polySBMA (5), uncrosslinked copolymer, poly(SBMA-co-MDOPA) (6), crosslinked zwitterionic polymer without MDOPA, poly(SBMA-co-PEGDMA) (7), were also prepared for comparison. After polymerization, the feed ratios of each monomer reflected the repeating unit ratios of copolymer 6 without a large discrepancy. The ultimate molar ratios between SBMA and MDOPA in the copolymer 6 was determined to be 86:14 based on $^1$H NMR peak integration of representative peaks for each repeating unit segment after polymerization. Unlike copolymer 6, calculation of accurate integration values for the series of terpolymers 4 based on $^1$H NMR spectra was technically difficult because of the error limits of $^1$H NMR instrument and signal overlays of multiple peaks from terpolymer structure. Thus, the terpolymers were designated as poly(MDOPA$_x$-co-SBMA$_y$-co-PEGDMA$_z$), where the letters x, y, and z represent the feed molar ratios between MDOPA, SBMA, and PEGDMA.

The desired terpolymers were obtained as dried, white fluffy solids after lyophilization as shown in the lower left corner of FIG. 1. For all of the prepared polymers, the ease of monomer preparation and simplicity of radical polymerization allowed for the facile production of multi-gram scale quantities of the desired polymers with reproducible quality. While the dried polymer itself displays no adhesion properties, swelling of the polymer samples with deionized water results in a tacky and highly viscous adhesive, with higher amounts of PEGDMA crosslinker leading to increasingly cohesive solid-like gels. The image in the bottom-right of FIG. 1 demonstrates the ease with which the swollen adhesive can be manipulated, even to the point of containing it in a syringe for ease of application to a targeted area.

Adhesion Property Measurement

Figures 3A, 3B, 3C:
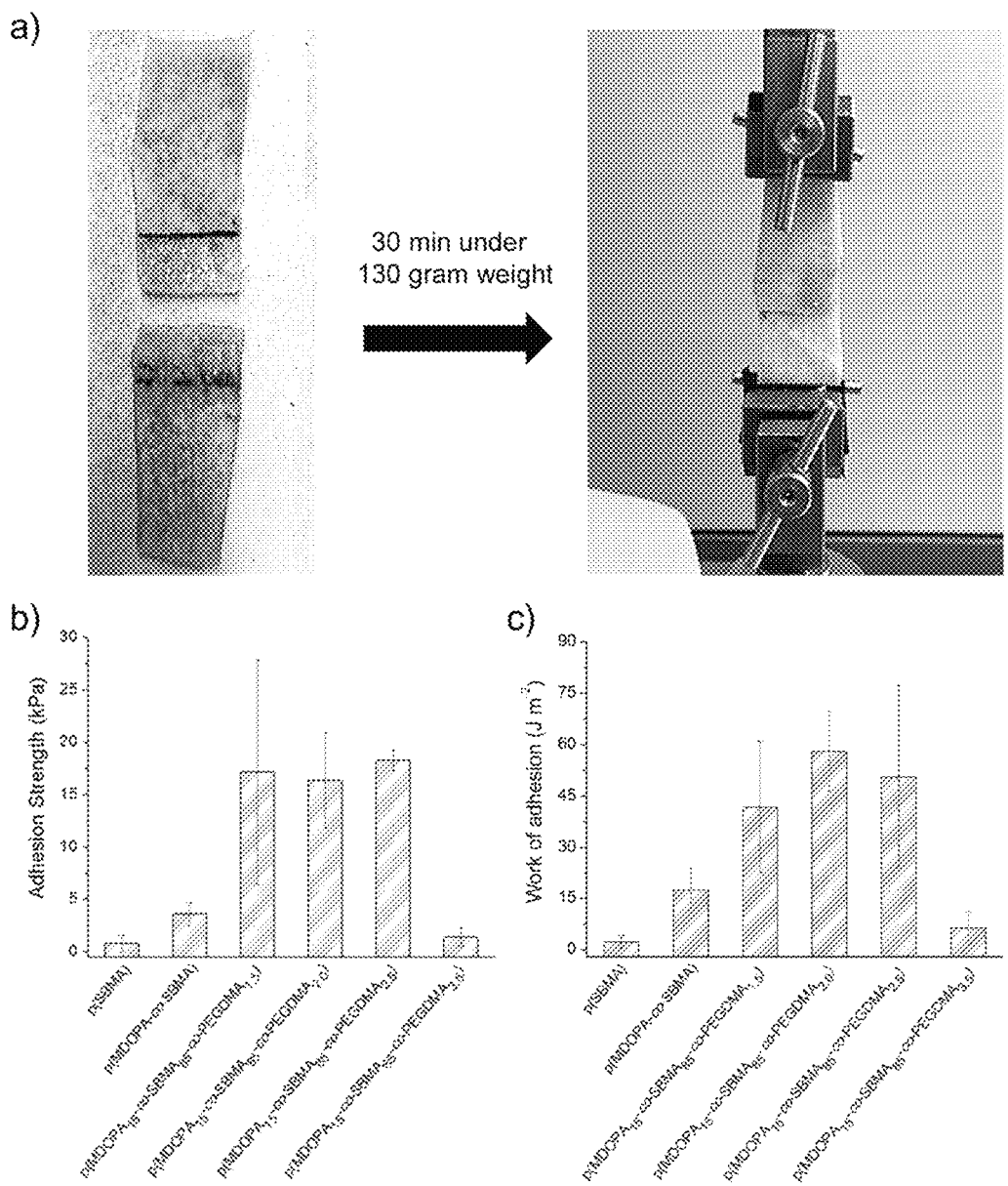
FIG. 3A shows photographs of lap shear tensile test setup; adhesive polymer was first applied on wet porcine skin, and applied region was overlaid, then the overlaid region was pressed for 30 min under 130 g of weight. Next, the prepared sample was mounted on sample grips at tensile tester. Maximum adhesion strength and work of adhesion for the polymers is shown in FIGS. 3B and 3C, respectively. The polymers are polySBMA, poly(MDOPA-co-SBMA), poly(MDOPA$_{15}$-co-SBMA$_{85}$-co-PEGDMA$_{1.5}$), poly(MDOPA$_{15}$-co-SBMA$_{85}$-co-PEGDMA$_{2.0}$), poly(MDOPA$_{15}$-co-SBMA$_{85}$-co-PEGDMA$_{2.5}$), and poly(MDOPA$_{15}$-co-SBMA$_{85}$-co-PEGDMA$_{3.5}$). The standard deviations (depicted as error bars) were calculated based on repeated measurements for each sample (measurements were repeated at least four times for each sample).

Adhesion properties of maximum adhesion strength and work of adhesion were obtained by lap shear strength test. In this adhesion test, porcine skin was selected as an adherent due to its biological similarity to human tissues (R. Kong, et al., *Analyst* 2011, 136, 2359-2366; A. M. Barbero, et al., *Toxicol. In Vitro* 2009, 23, 1-13). The prepared substrates, porcine skins, were wet with DI water prior to adhesive application. Then, water-swollen adhesive was placed on 2.0 cm×1.0 cm rectangle area of total 5.0 cm×2.0 cm sized porcine skin. The water-swollen adhesive was prepared by swelling dry adhesives (32.00 mg) with DI water (24.00 μL) for 4 hours. After that, the adhesive applied part was overlaid with another porcine skin pair, and then overlaid part was pressed for 30 min under ~130 grams of weight. Next, the prepared sample was mounted on a grip at tensile tester (FIG. 3A). The sample was pulled to failure with a crosshead speed 1 mm/min. The collected force vs. displacement curve was analyzed to get adhesion strength (kPa, dividing maximum force, Newton, by a contact area, m$^2$) and work of adhesion (J m$^{-2}$, dividing adhesion energy (Joule, integration of force vs. displacement curve) by a contact area, m$^2$). The test was repeated at least 5 times for each condition to get averages as well as standard deviations.

There could be elastic deformation of the tissue during the tensile test, implying that calculated work of adhesion may include the work originated from the elastic deformation of the tissue. The work of adhesions were used to compare tested samples that are prepared under the same condition without considering elastic deformation of the tissue substrate. All used porcine skin tissue samples were identical in terms of surface smoothness, thickness, flexibility, and size. For each polymer, lap shear strength was measured at least four times, and then averaged, and finally reported with error bars representing standard deviation. As shown in FIGS. 3B and 3C, the homo polySBMA exhibited very low adhesion strength and work of adhesion (0.8 kPa and 2.3 J m$^{-2}$, respectively). For the copolymer containing MDOPA, poly(MDOPA-co-SBMA), it showed increased adhesion strength and work of adhesion (3.6 kPa and 17.6 J m$^{-2}$, respectively) compared to polySBMA, indicating that the incorporation of MDOPA has enhanced the adhesion properties of the polymer. Detailed studies in mussel (e.g., common blue mussel *Mytilus edulis*) revealed that DOPA moiety in mussel foot proteins substantially contribute to wet adhesion of mussel to diverse inorganic (e.g., minerals and metal oxide surfaces) and organic substrates (e.g., biological tissues or polymeric surfaces) via bidentate coordination, covalent bonding, hydrogen bonding or hydrophobic interaction. (G. P. Maier, et al., Science 2015, 349, 628; P. Kord Forooshani, et al., *J. Polymer Sci. Part A: Polymer Chem.* 2017, 55, 9-33). The observed enhanced adhesion properties (adhesion strength and work of adhesion) of poly(MDOPA-co-SBMA) over pSBMA is owing to the newly generated bonds between DOPA moieties of the polymer and porcine skin.

In the case of the PEGDMA-crosslinked terpolymers containing MDOPA moiety, the adhesion strength and work of adhesion were substantially increased for poly(MDOPA$_{15}$-co-SBMA$_{85}$-co-PEGDMA$_{1.5}$) that includes 1.5% PEGDMA crosslinker (17.2 kPa and 41.8 J m$^{-2}$, respectively), poly(MDOPA$_{15}$-co-SBMA$_{85}$-co-PEGDMA$_{2.0}$) (16.4 kPa and 58.0 J m$^{-2}$, respectively), and poly(MDOPA$_{15}$-co-SBMA$_{85}$-co-PEGDMA$_{2.5}$) (18.3 kPa and 50.6 J m$^{-2}$, respectively) samples in comparison with those of not crosslinked copolymer, while decreased small values of adhesion strength and work of adhesion (1.4 kPa and 6.3 J m$^{-2}$, respectively) were observed in poly(MDOPA$_{15}$-co-SBMA$_{85}$-co-PEGDMA$_{3.5}$). This result reveals that using of crosslinker up to 2.5 mol % significantly strengthens the adhesion properties of the polymer, but adhesion properties severely decrease from 3.5 mol % usage of crosslinker. Poly(MDOPA$_{15}$-co-SBMA$_{85}$-co-PEGDMA$_{3.5}$) was a stiff gel-like substance, resulting in poor contact with the porcine skins. An ideally crosslinked adhesive displays strong resistance to internal energy dissipation and crack propagation during the debonding process (J. Asahara, et al., *J. Applied Polymer Sci.* 2003, 87, 1493-1499). In particular, lightly crosslinking in pressure-sensitive adhesives reduces internal motion of polymer matrix resulting in prevention of the failure of the polymer matrix during the debonding process. However, if the degree of crosslinking is too high then the crosslinking solidifies the adhesive due to highly restricted polymer chain mobility in the bond formation process, resulting in poor wettability to the substrate surface and poor tackiness (tack: the ability of a material to stick to a surface on momentary contact, and then to resist separation). The poor adhesion of adhesives polymers also can occur due to unsuccessful polymerization. The unsuccessful polymerization may result low yield as well as low molecular weight-polymers which lead low adhesion strength (G. Y. Choi, et al., *Langmuir* 1999, 15, 8447-8450). Although direct measurement of polymer molecular weight was not possible due to poor solubility of polymer in GPC solvents, based on obtained polymerization yield (ca. 66%) of poly(MDOPA$_{15}$-co-SBMA$_{85}$-co-PEGDMA$_{3.5}$), it is considered that polymerization occurred successfully. Thus, while note wishing to be bound by theory, it is believed that the main reason of the poor adhesion in poly(MDOPA$_{15}$-co-SBMA$_{85}$-co-PEGDMA$_{3.5}$) is the overly restricted polymer chain mobility originated from high degree of crosslinking not because of low molecular weight. Meanwhile, the crosslinking not only affect viscoelastic properties, but also molecular weight, size, and shape of polymer. The cross-linking of polymer generally results in hyper-branched polymers with broad molecular weight distributions. Experimental results have demonstrated that molecular weight impacts upon the bulk adhesion property of a polymer adhesives (longer molecules offer cohesion via chain entanglements, yet shorter chains bring surface wetting) (C. L. Jenkins, et al., *ACS Appl. Mater. Interfaces* 2013, 5, 5091-5096). For the synthesized terpolymer, poly(MDOPA-co-SBMA-co-PEGDMA), 1.5% to 2.5% crosslinker feeding demonstrates the best adhesion performance. The 3.5% and above crosslinker containing terpolymer is not an acceptable adhesive according to the obtained results in FIGS. 3B and 3C. After confirming that incorporation of MDOPA moiety and 1.5% to 2.5% crosslinker feeding significantly enhances the adhesion properties of the polymer adhesives, the adhesion strength and work of adhesion of poly(SBMA$_{100}$-co-PEGDMA$_{1.5}$), poly(SBMA$_{100}$-co-PEGDMA$_{2.0}$), and poly(SBMA$_{100}$-co-PEGDMA$_{2.5}$) was measured to investigate whether crosslinker alone sufficiently can improve the adhesion properties of the polymer adhesives or not. For the crosslinked polymers without MDOPA moiety, those polymers demonstrated very low adhesion strength and work of adhesion. The adhesion strength and work of adhesion of poly(SBMA$_{100}$-co-PEGDMA$_{1.5}$), poly(SBMA$_{100}$-co-PEGDMA$_{2.0}$), and poly(SBMA$_{100}$-co-PEGDMA$_{2.5}$) were measured to be "0.2 kPa and 0.7 J m$^{-2}$", "0.2 kPa and 0.3 J m$^{-2}$", and "0.2 kPa and 0.3 J m$^{-2}$", respectively. Because of very low adhesion strength of the polymers, the polymer-applied porcine skins were detached even before displacement reach to 10 mm. This result reveals that PEGDMA crosslinker alone cannot improve the adhesion properties of the pSBMA, and MDOPA is helpful for high adhesion strength and work of adhesion. Overall, the mechanical test results illustrate that both incorporation of MDOPA moiety and introduction of crosslinker are essential to achieve high adhesion strength and work of adhesion of polymer adhesives.

In Vitro Cytotoxicity Test

Cell morphology and proliferation HEK293A cells were assessed to test the cytotoxicity of the terpolymer. Human embryonic kidney (HEK) cell line is one of the most widely used lab human cell lines for assessing the cytotoxic effects of chemicals (V. Selvaraj, et al., *Intl. J. Nanomed.* 2014, 9, 1379; P. Lovecka, et al., *BioMed Res. Interl.* 2015, 2015). Cell morphology and proliferation HEK293A cells were assessed to investigate the cytotoxicity of the terpolymer. First, 250 mg of dried poly(MDOPA$_{15}$-co-SBMA$_{85}$-co-PEGDMA$_{1.5}$) was dissolved in 5 mL of DI water and then the pH of the solution was adjusted to 7.0 by adding 900 µL of 0.1 M NaOH, resulting in 42.3 mg/mL (250 mg of terpolymer in 5 mL of DI water and 0.9 mL of NaOH solution) polymer solution.

Then, the polymer solution was sterilized by UV treatment, because a non-UV treated sample demonstrated bacterial contamination. After the UV treatment, there was no evidence of bacterial contamination in cell culture medium DMEM supplemented with the terpolymer. During the UV treatment, polymer solutions were placed in Luzchem LCZ-4X photoreactor which was equipped with 14 bulbs (8 watts, 254 nm). Cell culture medium DMEM (ATTC, Dulbecco's Modified Eagle Medium) was mixed with this terpolymer solution at concentrations of 42, 419, and 3846 µg/mL by adding 1, 10, and 100 µL of the terpolymer stock solution into a 35 mm dish containing 1 mL DMEM supplemented with 10% FBS, respectively. Optical microscopy (DMI6000 B, Leica) was used to inspect cell morphology and proliferation after 48 hr incubation with the polymer. The same number of cells was seeded in each dish. For a quantitative analysis, the same number of cells were plated in eight 35 mm dishes. Four dishes were treated with 3,846 µg/mL terpolymer for 48 hours while the other 4 dishes were treated with the same volume of water and served as a control. Live cells from each dish were counted using a glass hemocytometer and cover slips after staining with trypan blue.

Figure 4:
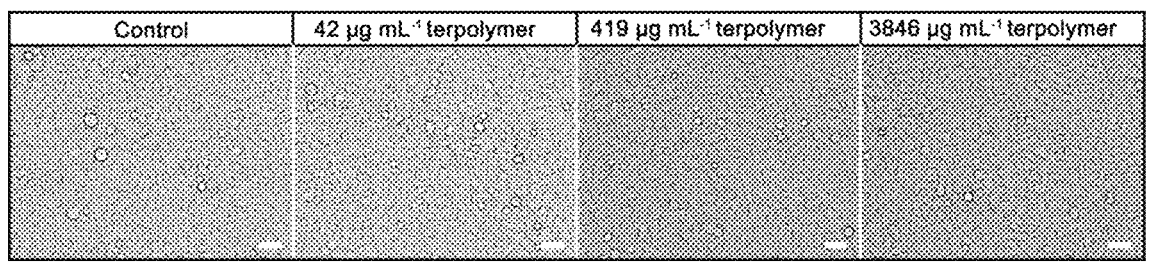
FIG. 4 shows live cell images of human embryonic kidney (293A-HEK) cells incubated with different concentrations of terpolymer 4 for 48 h; negative control and terpolymer 4 (42, 419, and 3846 μg mL$^{-1}$). Scale bars=50 μm.
Figure 5:
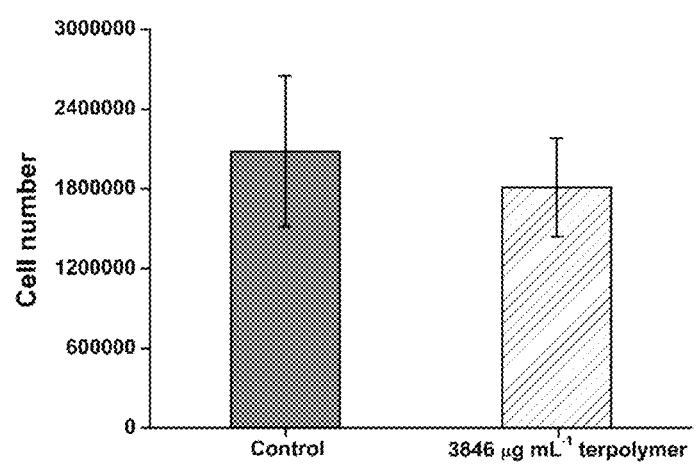
FIG. 5 shows number of HEK293A cells treated with terpolymer 4 (3846 μg mL$^{-1}$). Cells incubated without terpolymer 4 was used as a negative control. Value presents average cell number with ±standard deviation (represented as error bars) and each experiment was performed in quadruplicate.

As shown in FIG. 4, cells in the sample dishes with variable amounts of terpolymer solution were not appreciably different from those in the control dish without the terpolymer. FIG. 5 displays average cell number of HEK293A cells treated with the terpolymer at concentrations of 3846 µg/mL (ca. 1,812,500) and incubated without terpolymer (negative control, ca. 2,081,250) for 48 h. The calculated P value, ca. 0.22, demonstrates that there is no statistical significance between control and the tested terpolymer. If P>0.05, then statistically there is no significant difference between any data sets (N. Millar. *Sch. Sci. Rev.* 2001, 83, 23-34). Overall, cell morphology and proliferation results represent that the terpolymer adhesive is not cytotoxic.

Ex Vivo Anastomotic Leakage Prevention Test

The effectiveness of the disclosed terpolymer adhesives toward the prevention of anastomotic leakage in an ex vivo fashion were investigated. This experiment was conducted with fresh pig intestine obtained from a slaughtered pig within 24 hours. First, two separate intestinal tissues were sutured together according to a standard anastomosis surgical procedure. Then, methylene blue solution (5 mg of methylene blue/1 mL of DI water) was placed into the cavity of the sutured intestine followed by sealing both ends of the intestine (see FIGS. 6A and 6B). Next, sutured region was treated with water-swollen terpolymer adhesive. The used adhesive was 400 mg of dried poly(MDOPA$_{15}$-co-SBMA$_{85}$-co-PEGDMA$_{1.5}$) 4 in 0.4 mL of DI water. The terpolymer concentration in water is slightly less than those adhesives employed in adhesion test due to viscosity issue. Low concentration was required to extrude the polymer solution through a syringe tip. Finally, leakage of methylene blue solution was visually monitored. The control sample without applying the adhesive was also monitored under the identical condition. All these experiments were performed twice (single layer suturing method and double layer suturing method) and were monitored for two days (48 hours).

Figures 6A, 6B:
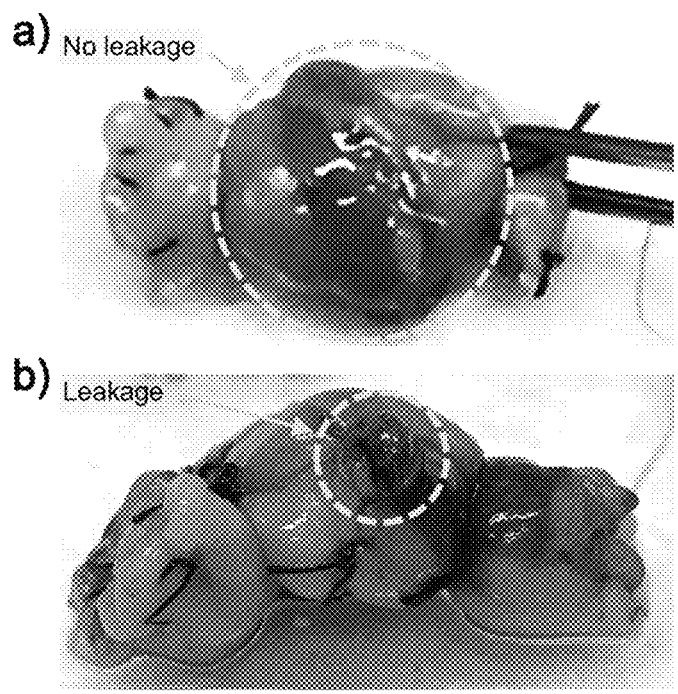
FIGS. 6A and 6B shows ex vivo anastomotic leakage prevention test on porcine intestine (FIG. 6A) with terpolymer adhesive 4 or (FIG. 6B) without adhesive.

Application of a solution of terpolymer 4 to the suture site completely prevents leakage of the dye from the sutures (FIG. 6A, purple colorations of the tissue is the result of methylene blue inside the tissue). Additionally, the methylene blue solution in the sutured intestine with terpolymer adhesive did not leak during the two-day (48 hours) monitoring. FIG. 6B shows an intestinal anastomosis which was not treated with terpolymer adhesive solution, resulting in obvious leakage of methylene blue from the anastomosis site. The same results were observed for both single layer and double layer suturing. FIGS. 6A and 6B visually illustrate the ability of a terpolymer adhesive as disclosed herein to provide a liquid-tight physical barrier against anastomotic leakage. The combination of the in vitro cell experiments and ex vivo anastomosis studies indicate that the disclosed terpolymer adhesives, e.g., poly(SBMA-co-MDOPA-co-PEGDMA), can be used for intestinal anastomosis to reduce incidents of potentially lethal anastomotic leakage and save medical costs associated with complications of the leakage.

Example 2: Crosslinked Photo-Responsive Polymers

Synthesis of Poly(MDOPA-co-SBMA-co-NBDM) (8)

In this designed crosslinking system, the crosslinking bonds can be cleaved via UV irradiation, freeing individual polymer strands and thereby weakening the cohesion of the entire polymer network. The weakened cohesion directly results in reduced adhesion properties. By using this principle, the crosslinking can be systematically controlled to adjust the adhesion strength of the polymer system.

Figure 7:
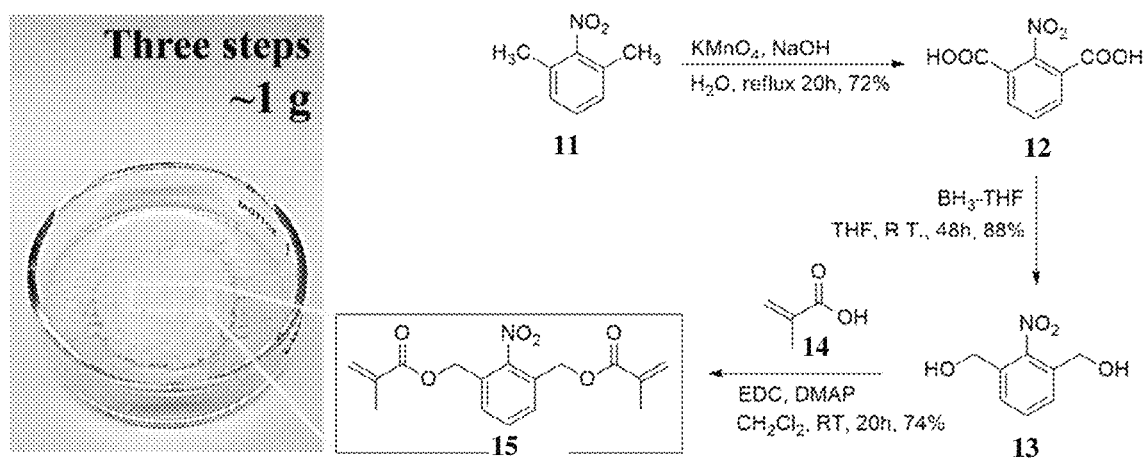
FIG. 7 shows a synthetic scheme and a photograph of a photocleavable cross-linker, 2-nitro-1,3-benzenedimethanol dimethacrylate (NBDM) 15.

The o-nitrobenzyl ester was used as the photocleavable moiety. Adjacent dimethacrylate moieties serve to integrate this monomer into the wider polymer network of other methacrylate monomers, effectively crosslinking the polymer chains during a thermally-initiated radical polymerization. The synthetic route toward photocleavable monomer, 2-nitro-1,3-benzenedimethanol dimethacrylate (NBDM) 15, is displayed in FIG. 7. First, 2-nitro-1,3-benzenedicarboxylic acid 12 and 2-nitro-1,3-benzenedimethanol 13 were synthesized sequentially according to reported methods (D. Han, et al., *Macromolecules*, 2011, 44, 437-439). Diacid 12 was prepared by oxidation of 1,3-dimethyl-2-nitrobenzene (11) using potassium permanganate. Then, diol 13 was produced by subsequent reduction of the resulting diacid (12). Esterification of diol 13 with methacrylic acid in the presence of N-(3-dimethylaminopropyl)-N'-ethylcarbodiimide hydrochloride (EDC.HCl) and 4-(dimethylamino)pyridine (DMAP) resulted in the desired compound 15, as a light yellow solid as shown in the left portion of FIG. 7.

Figure 8:
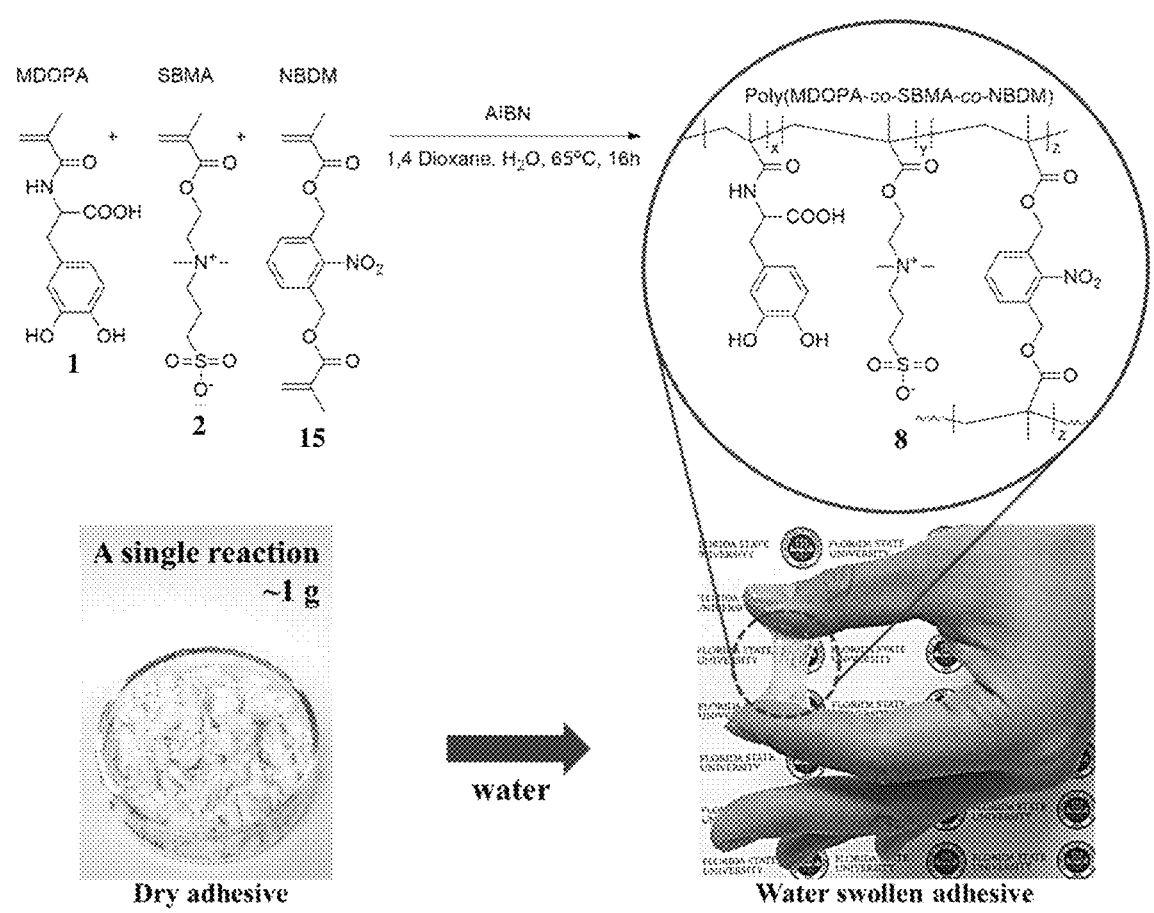
FIG. 8 shows a synthetic scheme and a photograph of photodegradable poly(MDOPA-co-SBMA-co-NBDM) 8. The repeating unit ratio of the prepared polymer is 10:87:3 (MDOPA:SBMA:NBDM).

Photodegradable poly(MDOPA-co-SBMA-co-NBDM) 8 was synthesized by a facile one-step thermally-initiated free radical polymerization of photocleavable cross-linker 15, N-methacryloyl-3,4-dihydroxyl-L-phenylalanine (MDOPA) 1, and SBMA 2 as illustrated in FIG. 8. Based on previously-reported studies which performed extensive adhesion tests to understand structure-property relationships on adhesion properties, the optimum molar monomer feed ratio of MDOPA, SBMA, and NBDM for preparing terpolymer 8 was determined to be 15:85:5. In particular, Wilker et. al. has thoroughly studied the effect of catechol groups on bulk adhesion properties with various molar ratios of catechol-containing monomers (C. R. Matos-Perez, et al., *J. Am. Chem. Soc.*, 2012, 134, 9498-9505). Poly(MDOPA-co-SBMA) 9 was also prepared as a control using the same monomer feed ratio as that of terpolymer 8, but without incorporation of NBDM. The final molar ratios of each segment (MDOPA, SBMA, and NBDM) in the polymers were determined by integration of the respective peaks in the $^1$H NMR spectra (FIG. 9) and the final molar ratio of MDOPA, SBMA, and NBDM in terpolymer 8 and bipolymer 9 were 10:87:3 and 10:90:0, respectively. Prior to polymerization, catechol-containing monomer 1 was prepared according to previously reported methods. As a zwitterionic monomer, 2 was chosen because of its chemical stability, commercial availability, and low cost (S. Jiang et al., *Adv. Mater.*, 2010, 22, 920-932; Q. Liu, et al., *J. Appl. Polym. Sci.*, 2014, 131, 40789-40797). The final polymer product was obtained after lyophilization and the resulting polymer was isolated as a light pink powder as shown in the lower left image of FIG. 8. It is worth noting that the ease of monomer preparation, and the simplicity of radical polymerization allowed for the facile production of multi-gram scale quantities of the desired terpolymer 8. Although the obtained dry polymer does not display adhesion properties, the solid polymer became a highly tacky and viscous gel-like material after having been swollen in ultra-pure deionized water. The water-swollen terpolymer exhibits definite adhesion properties to biological substrates, as the image in the lower-right of FIG. 8 demonstrates, implying that 8 possesses properties suitable for investigation as a biomedical adhesive.

Figure 9:
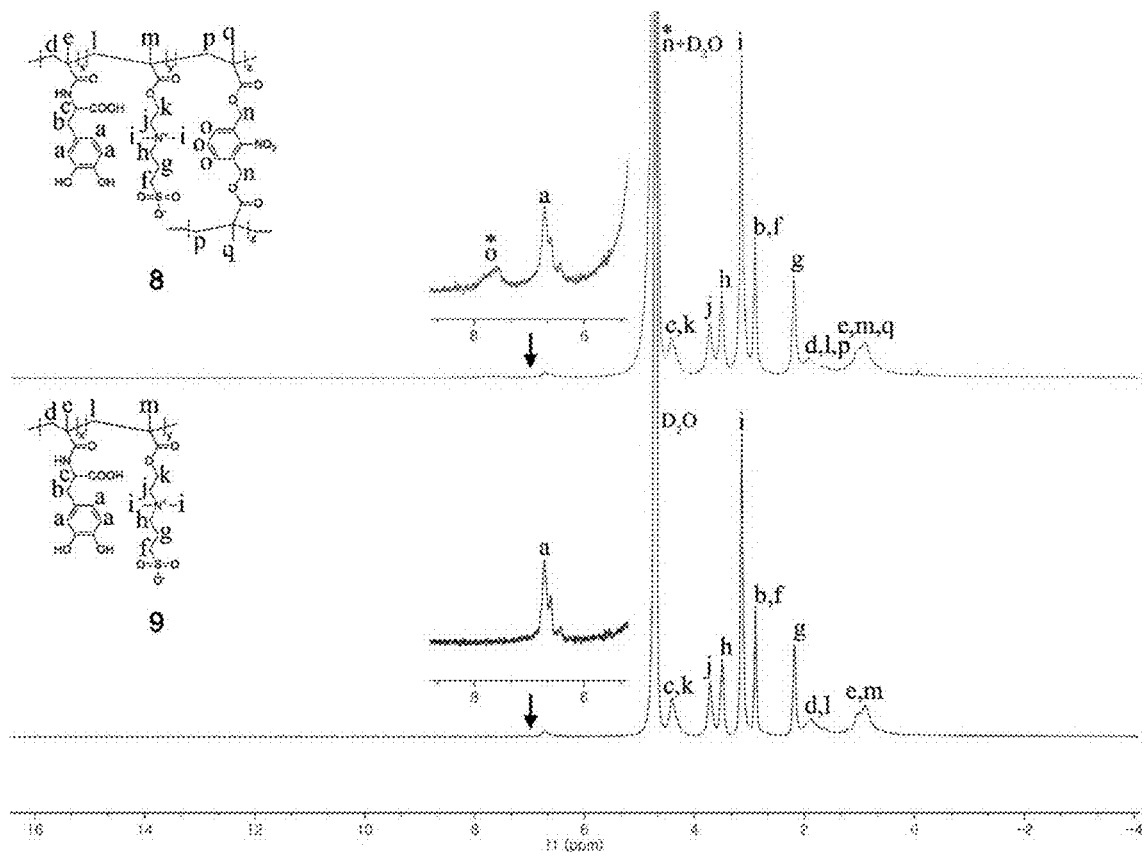
FIG. 9 shows $^1$H NMR spectra for photodegradable terpolymer 8 and poly(MDOPA-co-SBMA) 9. The repeating unit ratio of the prepared polymer 9 is 10:90 (MDOPA:SBMA).

The chemical structure of synthesized photodegradable terpolymer 8 was investigated by $^1$H NMR spectroscopy. As shown in FIG. 9, the $^1$H NMR spectra of 8 and 9 were obtained by dissolving ~3% crosslinked 8 and 0% crosslinked 9 in D$_2$O in a glass vial, respectively, and transferring the resulting solutions to NMR tubes for analysis. The $^1$H NMR spectra of both terpolymer 8 and bipolymer 9 clearly show the resonances ascribed from MDOPA 1 at 6.70, 2.88, and 4.39 ppm (resonances "a," "b," and "c") and from SBMA 2 at 2.88, 2.18, 3.49, 3.13, 3.70, and 4.39 ppm (resonances "f," "g," "h," "i," "j," and "k"), indicating successful incorporation of MDOPA and SBMA moieties in both polymers. The $^1$H NMR spectrum of photodegradable terpolymer 8 shows the additional aromatic protons derived from photocleavable cross-linker 15 at 7.54 ppm (resonance "o"; marked with a blue asterisk) revealing a successful incorporation of photocleavable cross-linker 15 into terpolymer 8.

Photoreaction Measurement

Figures 10A, 10B, 10C:
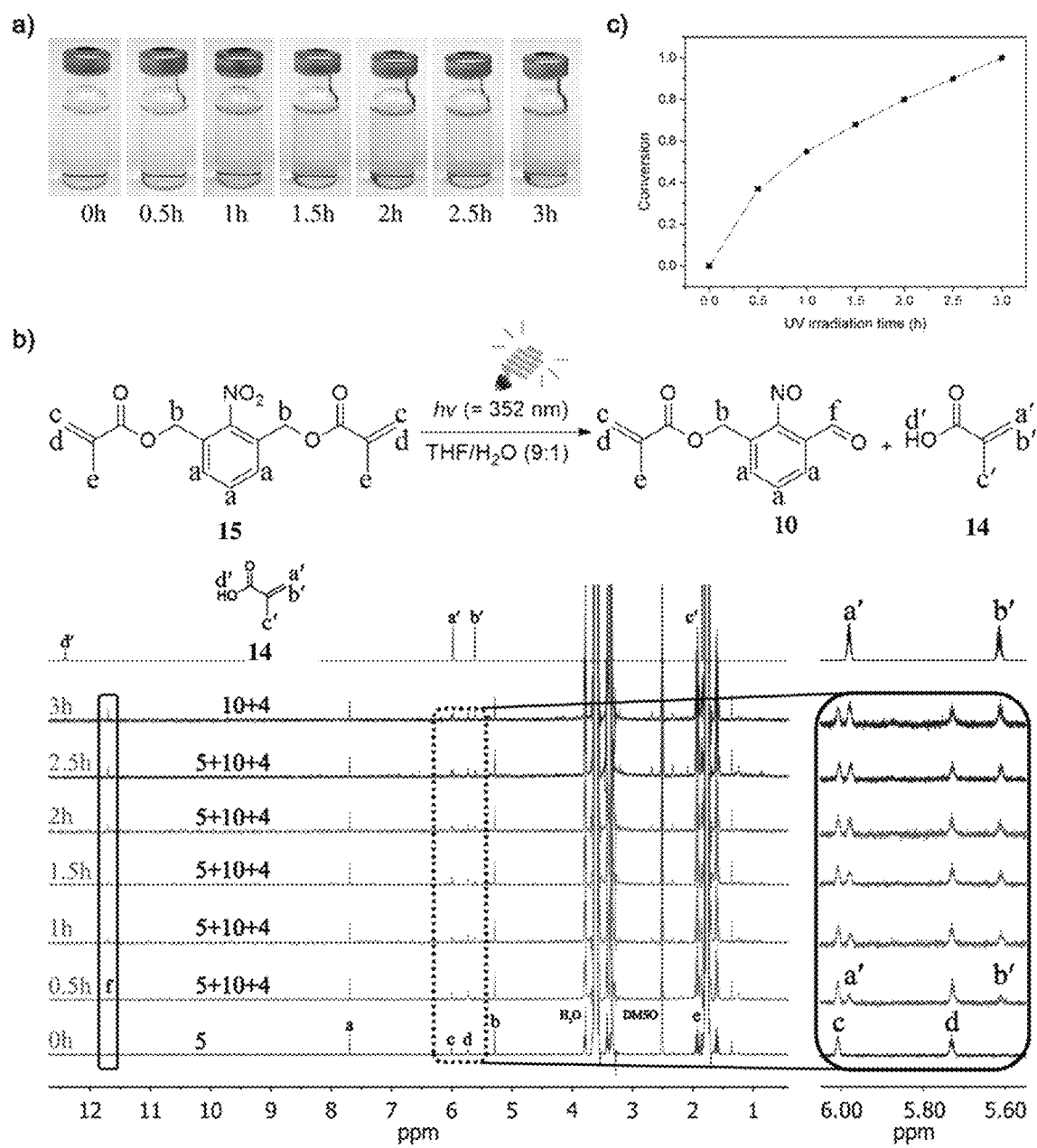
FIG. 10A shows photographs.
FIG. 10B shows $^1$H NMR spectra.
FIG. 10C shows a conversion plot of 15 to 10 and 14 over the course of UV irradiation. The conversions were determined by comparison of $^1$H NMR signals.

Proton NMR spectroscopy was used to monitor the reaction under UV irradiation in 30-minute increments. As shown in FIG. 10A, irradiation of 15 in a 90:10 THF:water (0.01 M) cosolvent solution at 352 nm for 30 minutes resulted in a light yellow solution. The solution gradually became a dark yellow color over the course of 3 hours, reflecting the cleavage of the 2-nitrobenzyl group with increased UV irradiation time (N. Kalva, et al., *Polym. Chem.*, 2015, 6, 6826-6835). Upon UV irradiation (0.5 hour), new signals appeared in the proton spectrum at 11.70, 5.98, and 5.61 ppm, ascribed to the newly created 2-nitrosobenzaldehyde 10 and methacrylic acid 14, respectively. These results are consistent with previously reported experimental results (A. M. Kloxin, et al., *Nat. Protoc.*, 2010, 5, 1867-1887) and the reported mechanism of the photocleavage of 2-nitrobenzyl esters (M. A. Azagarsamy, et al., *ACS Macro Lett.*, 2014, 3, 515-519; D. D. McKinnon, et al., *Biomacromolecules*, 2014, 15, 2808-2816; M. W. Tibbitt, et al., *Macromolecules*, 2013, 46, 2785-2792). Thus, the resonance at 11.70 ppm represents the aldehyde proton of compound 10. The newly appeared resonances at 11.70, 5.98, and 5.61 ppm continuously increased with increasing irradiation time, and the integration ratio between resonance c to a' reached a 1:1 level after 3 hours of UV irradiation, indicating complete consumption of crosslinker 5 according to previously published mechanistic information. Conversion of 15 to 10 and 14 over UV irradiation time was accurately calculated based on the integrations of signals c and a' (FIG. 10C; detailed calculation procedure is described in the Supporting Information). The obtained conversion curve shows that photocleavage occurred rapidly for the first 30 min and then continued at a slower rate until full conversion was achieved after 3 hours of irradiation.

Figures 11A, 11B:
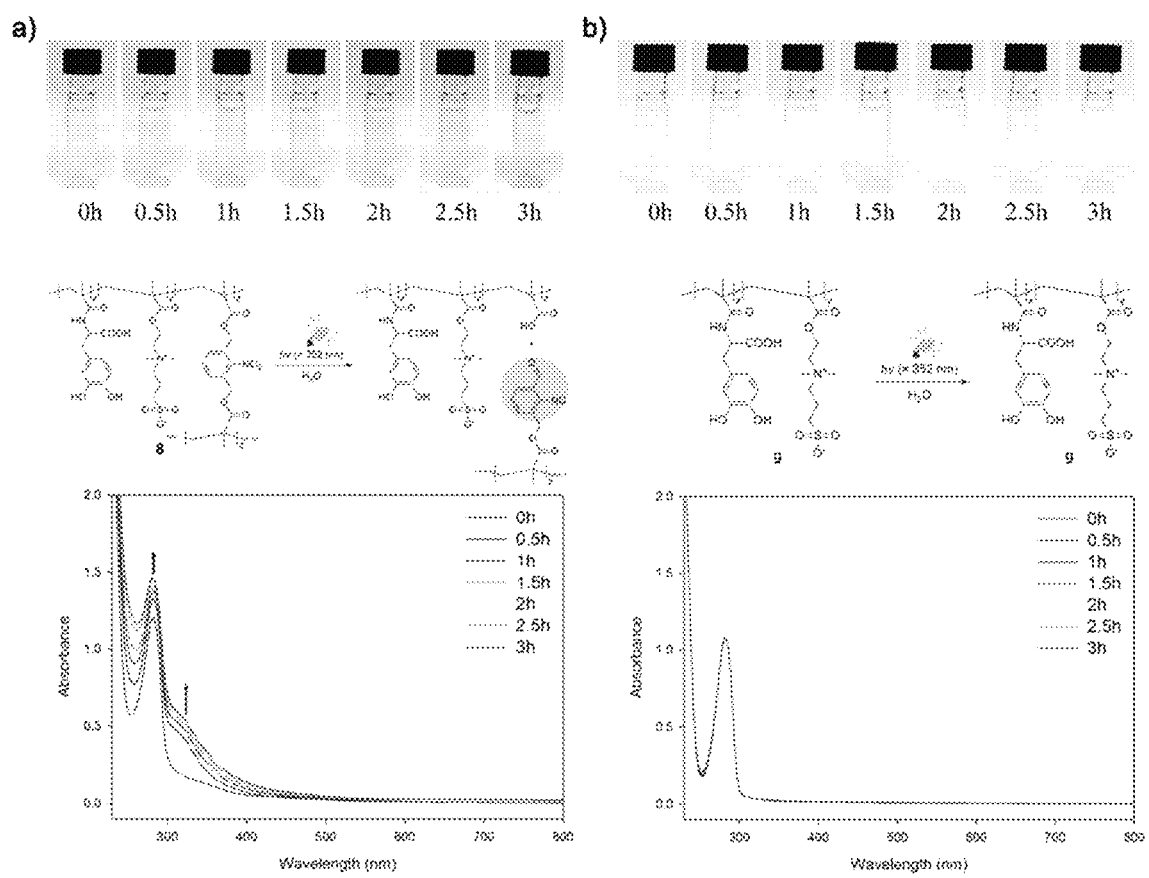
FIG. 11A shows photographs and UV/Vis spectra of aqueous photodegradable terpolymer 8 and FIG. 11B shows photographs and UV/Vis spectra of aqueous photodegradable copolymer 9 as a function of UV irradiation time.

Having investigated the photolysis characteristics of pristine crosslinker over UV irradiation time, the UV-vis spectra of the terpolymer was monitored over time in order to study the photocleavage behavior of the crosslinker-containing terpolymer. An aqueous solution of terpolymer 8 (0.1 wt %) was irradiated at 352 nm and then the resulting absorption spectra were recorded every 30 min. As shown in the top photograph of FIG. 11A, an obvious visible change was observed in solution as UV irradiation time was increased. The gradual color change in solution, from colorless to pale brown, implies that the cleavage of the incorporated 2-nitrobenzyl group in 8 increases over UV irradiation time. FIG. 11A displays UV/Vis spectra of the photodegradable terpolymer during UV irradiation. At t=0, the terpolymer 8 displays two absorption bands near 280 and 350 nm corresponding to the catechol (J. H. Ryu, et al., *Acta Biomater.*, 2015, 27, 101-115) and nitro functionalities (J. A. Johnson, et al., *Macromolecules*, 2007, 40, 3589-3598), indicating successful incorporation MDOPA and NBDM moieties in the terpolymer 8. During the course of UV irradiation, the absorptions of the 2-nitrosobenzaldehyde functionality (absorptions at 280 and 315 nm) (Y. V. Il'ichev, et al., *J. Am. Chem. Soc.*, 2004, 126, 4581-4595) gradually increase until 3 hours with irradiation time. The change in absorption at 350 nm was not identifiable during UV irradiation because the original absorption intensity was very weak. In addition, the nitro group absorption at 350 nm was hidden beneath the large growth of absorption intensity at 315 nm (nitrosobenzaldehyde). The significant absorption enhancement on 280 and 315 nm for 2-nitrosobenzaldehyde indicates that photodegradation of terpolymer 8 occurs relatively rapidly for the first 30 min and then gradually continued until the 3 hour mark. This result also implies that cross-linking density (number of cross-link points per unit volume of terpolymer 8) is greatly reduced within the first 30 minutes, then continues gradually reducing until 3 hours. In contrast, copolymer 9 having no photocleavable o-nitrobenzyl group does not show any color change in aqueous solution (0.1 wt %) under identical experimental conditions. These results indicate the observed absorption changes in terpolymer 8 are due to the photocleavage reaction of incorporated o-nitrobenzyl containing cross-linker 15.

Adhesion Property Measurement

Figures 12A, 12B, 12C, 12D:
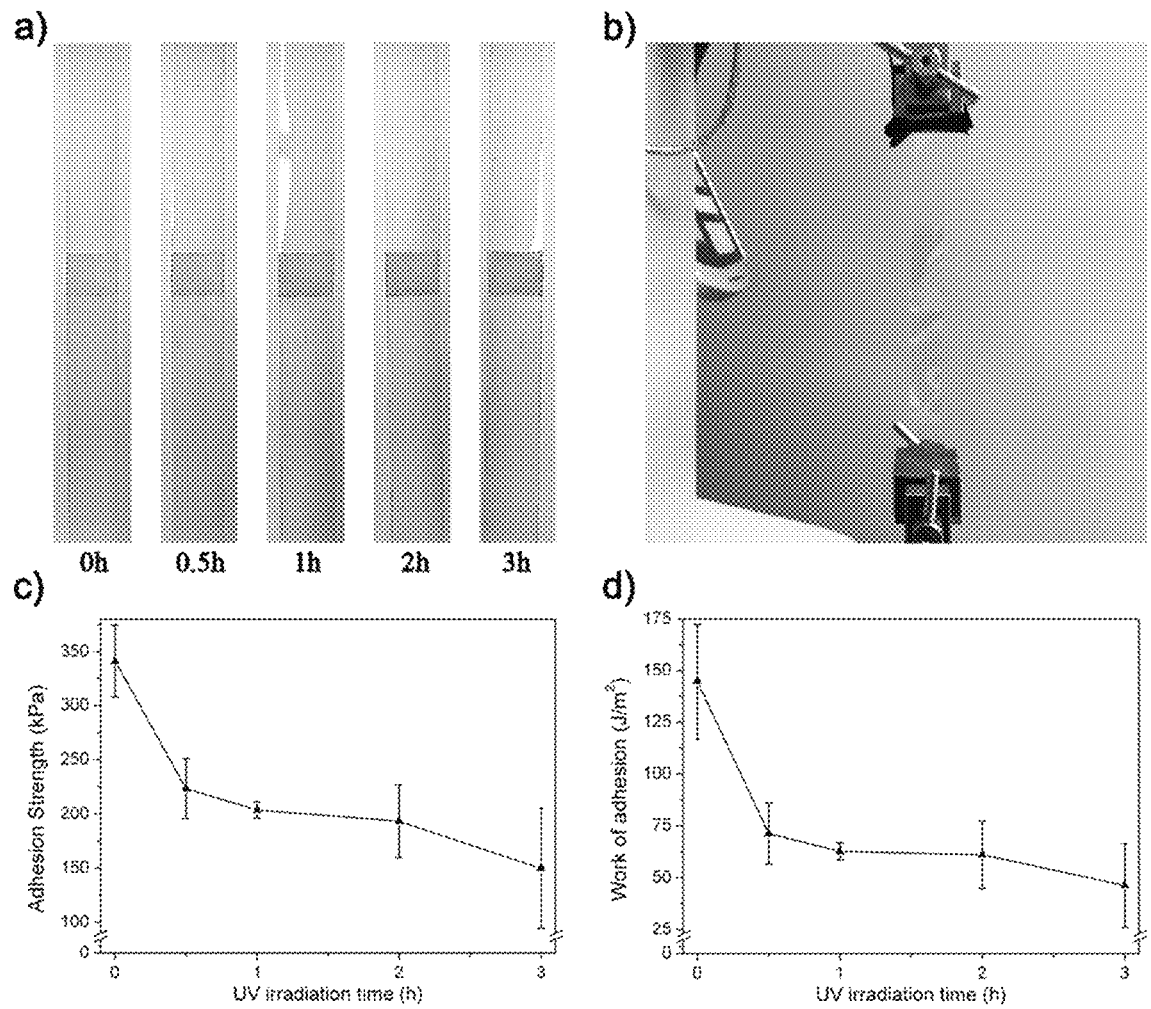
FIG. 12A shows photos of five adhesion testing samples with varying UV exposure time.
FIG. 12B shows a lap shear tensile testing apparatus.
FIG. 12C shows maximum adhesion strength vs. UV irradiation time.
FIG. 12D shows work of adhesion vs. UV irradiation time. Error bars represent standard deviation of five measurements per sample.

The mechanical properties of terpolymer 8 were quantified by measuring its adhesion strength as a function of UV irradiation time. These experiments were carried out via lap shear strength tests to investigate the effect of photodegredation on the adhesion strength of the developed polymer. In these experiments, five samples were prepared, as shown in FIG. 12A, in which the terpolymer-treated Mylar films were irradiated at 352 nm for 0, 0.5, 1, 2, and 3 hours, respectively. As irradiation time increased, the color of the adhesive joint gradually became a darker brown, reflecting the degradation of the adhesive upon UV irradiation. Then, the prepared Mylar film samples were mounted on a lap shear tensile testing apparatus (FIG. 12B) and pulled to failure. The obtained force vs. displacement curves were analyzed to determine adhesion strength (maximum force per unit area in a curve, kPa) and work of adhesion (integration of a curve per unit area, $J/m^2$). The test was repeated five times for each sample with the specified UV exposure time. The average value and standard deviation of adhesion strength and work of adhesion was calculated by using the obtained curves (force vs. displacement). As shown in FIGS. 12C and 12D, the terpolymer adhesive exhibited strong adhesion strength and a high work of adhesion (341 kPa and 144 $J/m^2$, respectively) before UV irradiation. The adhesion strength and work of adhesion were significantly reduced to 223 kPa and 71 $J/m^2$, respectively, (ca. 38 and 51% reduction, respectively) after only 30 minutes of UV irradiation. The adhesion strength and work of adhesion gradually decreased with irradiation time until the 3 hour mark. This result indicates that the force and energy required to debond the adhesive joint decreased rapidly until 30 min and then gradually thereafter by 3 h. Experimental results have demonstrated that as the crosslink density of the adhesive increases, the cohesive force of the terpolymer increases owing to the increase in formation of internal chemical bonds; in other words, the cohesion strength of the terpolymer adhesive decreases as crosslinking density decreases (X. Jin, et al., *Exp. Pol. Lett.*, 2009, 3, 814-820). From this perspective, a rapid reduction of both adhesion strength and work of adhesion results from the photodegredation of terpolymer 8.

It will be appreciated that variants of the above-disclosed and other features and functions, or alternatives thereof, may be combined into many other different systems or applications. Various presently unforeseen or unanticipated alternatives, modifications, variations, or improvements therein may be subsequently made by those skilled in the art which are also intended to be encompassed by the following claims.

What is claimed is:

1. An adhesive polymer comprising a catechol domain, a zwitterionic domain, and a crosslinking domain, wherein the crosslinking domain comprises a repeating unit having the structure

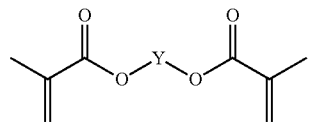

where Y is a polyethyleneoxide or polypropyleneoxide segment having a molecular weight from 50 to 5,000,000 daltons.

2. The adhesive polymer of claim 1, wherein the catechol domain comprises a repeating unit derived from the following monomer

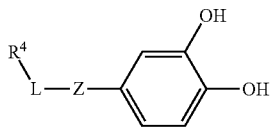

where Z is branched or straight chain alkyl, heteroalkyl, cycloalkyl, cycloheteroalkyl, aryl, or heteroaryl; L is a linker chosen from a bond, NH, O, C(O), C(O)O, or NH(CO); and $R^4$ is a polymerization group.

3. The adhesive polymer of claim 2, wherein the repeating unit is

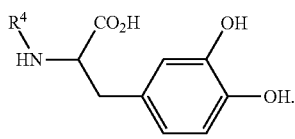

4. The adhesive polymer of claim 1, wherein the catechol domain comprises poly(N-methacryloyl-3,4-dihydroxyl-L-phenylalanine) (polyMDOPA).

5. The adhesive polymer of claim 1, wherein the catechol domain comprises from about 1 to about 50 mole % of the polymer.

6. The adhesive polymer of claim 1, wherein the zwitterionic domain comprises a repeating unit derived from one of the following monomers

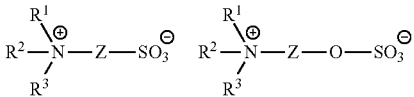

where Z is branched or straight chain alkyl, heteroalkyl, cycloalkyl, cycloheteroalkyl, aryl, or heteroaryl; $R^1$ is H, alkyl, heteroalkyl, cycloalkyl, heterocycloalkyl, aryl, or heteroaryl; and $R^2$ and $R^3$, are independently chosen from alkyl, heteroalkyl, cycloalkyl, heterocycloalkyl, aryl, or heteroaryl; wherein one or more of $R^1$, $R^2$, $R^3$, and Z are substituted with a polymerization group.

7. The adhesive polymer of claim 1, wherein the zwitterionic domain comprises poly(sulfobetaine methacrylate) (polySBMA).

8. The adhesive polymer of claim 1, wherein the zwitterionic domain comprises from about 70 to about 99 mole % of the polymer.

9. The adhesive polymer of claim 1, wherein the cross-linking domain comprises less than about 3.5 mole % of the polymer.

10. The adhesive polymer of claim 1, wherein the cross-linking domain comprises from about 1.5 to about 2.5 mole % of the polymer.

11. The adhesive polymer of claim 1, wherein the molar ratio of catechol domain to zwitterionic domain is from 1:99 to 30:70.

12. The adhesive polymer of claim 1, wherein the molar ratio of catechol domain to zwitterionic domain is 15:85.

13. The adhesive polymer of claim 1, wherein the polymer is a poly(N-methacryloyl-3,4-dihydroxyl-L-phenylalanine-co-sulfobetaine methacrylate-co-poly(ethylene glycol) dimethacrylate) (poly(MDOPA-co-SBMA-co-PEGDMA).

14. A method of closing a wound, comprising contacting the wound with a composition of claim 1.

* * * * *